US012653670B2

(12) United States Patent

Gurovich et al.

(10) Patent No.: US 12,653,670 B2
(45) Date of Patent: Jun. 16, 2026

(54) TRANSCATHETER HEART VALVE DELIVERY SYSTEMS AND METHODS

(71) Applicant: Edwards Lifesciences Corporation, Irvine, CA (US)

(72) Inventors: Nikolay Gurovich, Hadera (IL); Michael Bukin, Pardes Hanna (IL); Elena Sherman, Pardes Hana (IL); Alexey Tsypenyuk, Draper, UT (US)

(73) Assignee: Edwards Lifesciences Corporation, Irvine, CA (US)

( * ) Notice: Subject to any disclaimer, the term of this patent is extended or adjusted under 35 U.S.C. 154(b) by 1118 days.

(21) Appl. No.: 17/670,290

(22) Filed: Feb. 11, 2022

(65) Prior Publication Data

US 2022/0160507 A1 May 26, 2022

Related U.S. Application Data

(63) Continuation of application No. PCT/US2020/044994, filed on Aug. 5, 2020.

(60) Provisional application No. 62/886,677, filed on Aug. 14, 2019.

(51) Int. Cl.
*A61F 2/24* (2006.01)

(52) U.S. Cl.
CPC .......... *A61F 2/2436* (2013.01); *A61F 2/2418* (2013.01); *A61F 2/2433* (2013.01); *A61F 2250/0058* (2013.01)

(58) Field of Classification Search
CPC ............................... A61F 2/2418; A61F 2/915
See application file for complete search history.

(56) References Cited

U.S. PATENT DOCUMENTS

| | | | |
|---|---|---|---|
| 519,297 | A | 5/1894 | Bauer |
| 3,409,013 | A | 11/1968 | Berry |
| 3,548,417 | A | 12/1970 | Kisher |
| 3,587,115 | A | 6/1971 | Shiley |

(Continued)

FOREIGN PATENT DOCUMENTS

| | | |
|---|---|---|
| DE | 0144167 C | 9/1903 |
| DE | 2246526 A1 | 3/1973 |

(Continued)

OTHER PUBLICATIONS

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

(Continued)

*Primary Examiner* — Christopher D. Prone
(74) *Attorney, Agent, or Firm* — Klarquist Sparkman LLP

(57) ABSTRACT

A prosthetic heart valve and delivery device for delivering the prosthetic heart valve to a target implantation site, which reduce contact between the prosthetic heart valve and a delivery sheath through which the delivery device is advanced to the target implantation site, is disclosed. As one example, a prosthetic heart valve may comprise a frame including a first end with a plurality of apices spaced apart from one another around a circumference of the first end and a cover element covering the plurality of apices. The cover element may include a cushioning element or a bio-resorbable element.

15 Claims, 12 Drawing Sheets

(56)　　　　　References Cited

U.S. PATENT DOCUMENTS

| | | | |
|---|---|---|---|
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,955,895 A | 9/1990 | Sugiyama et al. |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,176,698 A | 1/1993 | Burns et al. |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,325,845 A | 7/1994 | Adair |
| 5,332,402 A | 7/1994 | Teitelbaum |
| 5,358,496 A | 10/1994 | Ortiz et al. |
| 5,360,444 A | 11/1994 | Kusuhara |
| 5,370,685 A | 12/1994 | Stevens |
| 5,397,351 A | 3/1995 | Pavonik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,599,305 A | 2/1997 | Hermann et al. |
| 5,607,464 A | 3/1997 | Trescony et al. |
| 5,609,626 A | 3/1997 | Quijano et al. |
| 5,628,792 A | 5/1997 | Lentell |
| 5,632,760 A | 5/1997 | Sheiban et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,782,809 A | 7/1998 | Umeno et al. |
| 5,800,508 A | 9/1998 | Goicoechea et al. |
| 5,824,044 A | 10/1998 | Quiachon et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,908,405 A | 6/1999 | Imran et al. |
| 5,916,147 A | 6/1999 | Boury |
| 5,925,063 A | 7/1999 | Khosravi |
| 5,944,690 A | 8/1999 | Falwell et al. |
| 5,957,949 A | 9/1999 | Leonhardt et al. |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,027,525 A | 2/2000 | Suh et al. |
| 6,033,381 A | 3/2000 | Kontos |
| 6,132,473 A | 10/2000 | Williams et al. |
| 6,143,016 A | 11/2000 | Bleam et al. |
| 6,162,208 A | 12/2000 | Hipps |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,235,050 B1 | 5/2001 | Quiachon et al. |
| 6,245,102 B1 | 6/2001 | Jayaraman |
| 6,251,092 B1 | 6/2001 | Qin et al. |
| 6,299,637 B1 | 10/2001 | Shaolian et al. |
| 6,302,906 B1 | 10/2001 | Goicoechea et al. |
| 6,338,740 B1 * | 1/2002 | Carpentier ........... A61F 2/2427 |
| | | 623/2.12 |
| 6,350,277 B1 | 2/2002 | Kocur |
| 6,352,547 B1 | 3/2002 | Brown et al. |
| 6,379,372 B1 | 4/2002 | Dehdashtian et al. |
| 6,383,171 B1 | 5/2002 | Gifford et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,471,672 B1 | 10/2002 | Brown et al. |
| 6,482,228 B1 | 11/2002 | Norred |
| 6,488,704 B1 | 12/2002 | Connelly et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,569,196 B1 | 5/2003 | Vesely |
| 6,579,305 B1 | 6/2003 | Lashinski |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |

(56) References Cited

U.S. PATENT DOCUMENTS

| | | | |
|---|---|---|---|
| 6,733,525 B2 | 5/2004 | Yang et al. | |
| 6,764,504 B2 | 7/2004 | Wang et al. | |
| 6,767,362 B2 | 7/2004 | Schreck | |
| 6,769,161 B2 | 8/2004 | Brown et al. | |
| 6,783,542 B2 | 8/2004 | Eidenschink | |
| 6,830,584 B1 | 12/2004 | Seguin | |
| 6,878,162 B2 | 4/2005 | Bales et al. | |
| 6,893,460 B2 | 5/2005 | Spenser et al. | |
| 6,908,481 B2 | 6/2005 | Cribier | |
| 6,936,067 B2 | 8/2005 | Buchanan | |
| 7,011,094 B2 | 3/2006 | Rapacki et al. | |
| 7,018,406 B2 | 3/2006 | Seguin et al. | |
| 7,018,408 B2 | 3/2006 | Bailey et al. | |
| 7,096,554 B2 | 8/2006 | Austin et al. | |
| 7,137,993 B2 | 11/2006 | Acosta et al. | |
| 7,225,518 B2 | 6/2007 | Eidenschink et al. | |
| 7,276,078 B2 | 10/2007 | Spenser et al. | |
| 7,276,084 B2 | 10/2007 | Yang et al. | |
| 7,316,710 B1 | 1/2008 | Cheng et al. | |
| 7,318,278 B2 | 1/2008 | Zhang et al. | |
| 7,320,702 B2 | 1/2008 | Hammersmark et al. | |
| 7,320,704 B2 | 1/2008 | Lashinski et al. | |
| 7,374,571 B2 | 5/2008 | Pease et al. | |
| 7,393,360 B2 | 7/2008 | Spenser et al. | |
| 7,435,257 B2 | 10/2008 | Lashinski et al. | |
| 7,462,191 B2 | 12/2008 | Spenser et al. | |
| 7,510,575 B2 | 3/2009 | Spenser et al. | |
| 7,563,280 B2 | 7/2009 | Anderson et al. | |
| 7,585,321 B2 | 9/2009 | Cribier | |
| 7,594,926 B2 | 9/2009 | Linder et al. | |
| 7,597,709 B2 | 10/2009 | Goodin | |
| 7,618,446 B2 | 11/2009 | Andersen et al. | |
| 7,618,447 B2 | 11/2009 | Case et al. | |
| 7,655,034 B2 | 2/2010 | Mitchell et al. | |
| 7,780,723 B2 | 8/2010 | Taylor | |
| 7,785,366 B2 | 8/2010 | Maurer et al. | |
| 7,959,661 B2 | 6/2011 | Hijlkema et al. | |
| 7,959,665 B2 | 6/2011 | Pienknagura | |
| 7,959,672 B2 | 6/2011 | Salahieh et al. | |
| 7,993,394 B2 | 8/2011 | Hariton et al. | |
| 8,029,556 B2 | 10/2011 | Rowe | |
| 8,075,611 B2 | 12/2011 | Millwee et al. | |
| 8,128,686 B2 | 3/2012 | Paul, Jr. et al. | |
| 8,167,932 B2 | 5/2012 | Bourang et al. | |
| 8,291,570 B2 | 10/2012 | Eidenschink et al. | |
| RE43,882 E | 12/2012 | Hopkins et al. | |
| 8,348,998 B2 | 1/2013 | Pintor et al. | |
| 8,449,606 B2 | 5/2013 | Ellasen et al. | |
| 8,454,685 B2 | 6/2013 | Hariton et al. | |
| 8,475,523 B2 | 7/2013 | Duffy | |
| 8,568,472 B2 | 10/2013 | Marchand et al. | |
| 8,652,203 B2 | 2/2014 | Quadri et al. | |
| 8,685,055 B2 | 4/2014 | VanTassel et al. | |
| 8,747,463 B2 | 6/2014 | Fogarty et al. | |
| 9,061,119 B2 | 6/2015 | Le et al. | |
| 9,078,781 B2 | 7/2015 | Ryan et al. | |
| 9,119,716 B2 | 9/2015 | Lee et al. | |
| 9,795,477 B2 | 10/2017 | Tran et al. | |
| 11,273,038 B2 | 3/2022 | Tang et al. | |
| 2001/0002445 A1 | 5/2001 | Vesely | |
| 2001/0007082 A1 | 7/2001 | Dusbabek et al. | |
| 2001/0021872 A1 | 9/2001 | Bailey et al. | |
| 2002/0026094 A1 | 2/2002 | Roth | |
| 2002/0032481 A1 | 3/2002 | Gabbay | |
| 2002/0058995 A1 | 5/2002 | Stevens | |
| 2002/0138135 A1 | 9/2002 | Duerig et al. | |
| 2002/0143390 A1 | 10/2002 | Ishii | |
| 2002/0165461 A1 | 11/2002 | Hayzelden et al. | |
| 2002/0173842 A1 | 11/2002 | Buchanan | |
| 2003/0014105 A1 | 1/2003 | Cao | |
| 2003/0040791 A1 | 2/2003 | Oktay | |
| 2003/0040792 A1 | 2/2003 | Gabbay | |
| 2003/0050694 A1 | 3/2003 | Yang et al. | |
| 2003/0100939 A1 | 5/2003 | Yodfat et al. | |
| 2003/0120341 A1 | 6/2003 | Shennib et al. | |
| 2003/0158597 A1 | 8/2003 | Quiachon et al. | |
| 2003/0212454 A1 | 11/2003 | Scott et al. | |
| 2004/0024452 A1 | 2/2004 | Kruse et al. | |
| 2004/0039436 A1 | 2/2004 | Spenser et al. | |
| 2004/0078074 A1 | 4/2004 | Anderson et al. | |
| 2004/0093061 A1 | 5/2004 | Acosta et al. | |
| 2004/0133263 A1 | 7/2004 | Dusbabek et al. | |
| 2004/0143197 A1 | 7/2004 | Soukup et al. | |
| 2004/0186558 A1 | 9/2004 | Pavonik et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0010285 A1 | 1/2005 | Lambrecht et al. | |
| 2005/0075725 A1 | 4/2005 | Rowe | |
| 2005/0075728 A1 | 4/2005 | Nguyen et al. | |
| 2005/0080474 A1 | 4/2005 | Andreas et al. | |
| 2005/0096736 A1 | 5/2005 | Osse et al. | |
| 2005/0096738 A1 | 5/2005 | Call et al. | |
| 2005/0137686 A1 | 6/2005 | Salahieh et al. | |
| 2005/0137689 A1 | 6/2005 | Salahieh et al. | |
| 2005/0149160 A1 | 7/2005 | McFerran | |
| 2005/0188525 A1 | 9/2005 | Weber et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2005/0245894 A1 | 11/2005 | Zadno-Azizi | |
| 2006/0004469 A1 | 1/2006 | Sokel | |
| 2006/0025857 A1 | 2/2006 | Bergheim et al. | |
| 2006/0058872 A1 | 3/2006 | Salahieh et al. | |
| 2006/0074484 A1 | 4/2006 | Huber | |
| 2006/0108090 A1 | 5/2006 | Ederer et al. | |
| 2006/0149350 A1 | 7/2006 | Patel et al. | |
| 2006/0183383 A1 | 8/2006 | Asmus et al. | |
| 2006/0229719 A1 | 10/2006 | Marquez et al. | |
| 2006/0259136 A1 | 11/2006 | Nguyen et al. | |
| 2006/0259137 A1 | 11/2006 | Artof et al. | |
| 2006/0282150 A1 | 12/2006 | Olson et al. | |
| 2006/0287717 A1 | 12/2006 | Rowe et al. | |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0073389 A1 | 3/2007 | Bolduc et al. | |
| 2007/0088431 A1 | 4/2007 | Bourang et al. | |
| 2007/0100356 A1 | 5/2007 | Lucatero et al. | |
| 2007/0112422 A1 | 5/2007 | Dehdashtian | |
| 2007/0162102 A1 | 7/2007 | Ryan et al. | |
| 2007/0203503 A1 | 8/2007 | Salahieh et al. | |
| 2007/0203575 A1 | 8/2007 | Forster et al. | |
| 2007/0203576 A1 | 8/2007 | Lee et al. | |
| 2007/0208550 A1 | 9/2007 | Cao et al. | |
| 2007/0213813 A1 | 9/2007 | Von Segesser et al. | |
| 2007/0219612 A1 | 9/2007 | Andreas et al. | |
| 2007/0233228 A1 | 10/2007 | Eberhardt et al. | |
| 2007/0239254 A1 | 10/2007 | Chia et al. | |
| 2007/0244546 A1 | 10/2007 | Francis | |
| 2007/0260305 A1 | 11/2007 | Drews et al. | |
| 2007/0265700 A1 | 11/2007 | Eliasen et al. | |
| 2008/0021546 A1 | 1/2008 | Patz et al. | |
| 2008/0065011 A1 | 3/2008 | Marchand et al. | |
| 2008/0103520 A1 | 5/2008 | Selkee | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0183271 A1 | 7/2008 | Frawley et al. | |
| 2008/0208327 A1 | 8/2008 | Rowe | |
| 2008/0243245 A1 | 10/2008 | Thambar et al. | |
| 2008/0255660 A1 | 10/2008 | Guyenot et al. | |
| 2008/0275537 A1 | 11/2008 | Limon | |
| 2008/0294230 A1 | 11/2008 | Parker | |
| 2008/0294248 A1 | 11/2008 | Yang et al. | |
| 2009/0024428 A1 | 1/2009 | Hudock, Jr. | |
| 2009/0069889 A1 | 3/2009 | Suri et al. | |
| 2009/0118826 A1 | 5/2009 | Khaghani | |
| 2009/0125118 A1 | 5/2009 | Gong | |
| 2009/0138079 A1 | 5/2009 | Tuval et al. | |
| 2009/0157175 A1 | 6/2009 | Benichou | |
| 2009/0192585 A1 | 7/2009 | Bloom et al. | |
| 2009/0228093 A1 | 9/2009 | Taylor et al. | |
| 2009/0276040 A1 | 11/2009 | Rowe et al. | |

(56) References Cited

U.S. PATENT DOCUMENTS

| | | |
|---|---|---|
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0299456 A1 | 12/2009 | Melsheimer |
| 2009/0319037 A1 | 12/2009 | Rowe et al. |
| 2010/0004735 A1 | 1/2010 | Yang et al. |
| 2010/0030318 A1 | 2/2010 | Berra |
| 2010/0036472 A1 | 2/2010 | Papp |
| 2010/0036473 A1 | 2/2010 | Roth |
| 2010/0042719 A1 | 2/2010 | Kinoshita |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0082094 A1 | 4/2010 | Quadri et al. |
| 2010/0094394 A1 | 4/2010 | Beach et al. |
| 2010/0100176 A1 | 4/2010 | Elizondo et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0168844 A1 | 7/2010 | Toomes et al. |
| 2010/0174363 A1 | 7/2010 | Castro |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2010/0274344 A1 | 10/2010 | Dusbabek et al. |
| 2011/0015729 A1 | 1/2011 | Jimenez et al. |
| 2011/0022157 A1 | 1/2011 | Essinger et al. |
| 2011/0054596 A1 | 3/2011 | Taylor |
| 2011/0066224 A1 | 3/2011 | White |
| 2011/0137331 A1 | 6/2011 | Walsh et al. |
| 2011/0137397 A1 | 6/2011 | Chau et al. |
| 2011/0160846 A1 | 6/2011 | Bishop et al. |
| 2011/0218619 A1 | 9/2011 | Benichou et al. |
| 2011/0319991 A1 | 12/2011 | Hariton et al. |
| 2012/0030090 A1 | 2/2012 | Johnston et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0239142 A1 | 9/2012 | Liu et al. |
| 2012/0259409 A1 | 10/2012 | Nguyen et al. |
| 2013/0023985 A1 | 1/2013 | Khairkhahan et al. |
| 2013/0030519 A1 | 1/2013 | Tran et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0214158 A1 | 7/2014 | Board et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0374802 A1 | 12/2016 | Levi et al. |
| 2017/0014229 A1 | 1/2017 | Nguyen-Thien-Nhon et al. |
| 2017/0065415 A1 | 3/2017 | Rupp et al. |
| 2018/0028310 A1 | 2/2018 | Gurovich et al. |
| 2018/0055629 A1 | 3/2018 | Oba et al. |
| 2018/0153689 A1 | 6/2018 | Maimon et al. |
| 2018/0228610 A1* | 8/2018 | Lashinski ............. A61F 2/2466 |
| 2018/0325665 A1 | 11/2018 | Gurovich et al. |
| 2018/0344456 A1 | 12/2018 | Barash et al. |
| 2019/0159894 A1 | 5/2019 | Levi et al. |
| 2019/0192288 A1 | 6/2019 | Levi et al. |
| 2019/0192289 A1 | 6/2019 | Levi et al. |
| 2019/0192296 A1 | 6/2019 | Schwartz et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0592410 B1 | 10/1995 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| JP | 2010042719 A | 2/2010 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9912483 A1 | 3/1999 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 02060352 | 8/2002 |
| WO | 03030776 A2 | 4/2003 |
| WO | 03047468 | 6/2003 |
| WO | 2004019825 A1 | 3/2004 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |

(56)                    References Cited

FOREIGN PATENT DOCUMENTS

| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | 2013106585 | A1 | 7/2013 |
| WO | 2015085218 | A1 | 6/2015 |
| WO | 2019144036 | A1 | 7/2019 |

OTHER PUBLICATIONS

Bailey, S. "Percutaneous Expandable Prosthetic Valves," Textbook of Interventional Cardiology vol. 2, 2nd Ed. pp. 1268-1276. 1994.

Fontaine, M.D., Arthur B., et al., "Prototype Stent: Invivo Swine Studies in the Billary System1", p. 101-105, Journal of Vascular and Interventional Radiology; Jan.-Feb. 1997; vol. 8, No. 1.

Fontaine, M.D., Arthur B., et al, "Vascular Stent Prototype; Results of Preclinical Evaluation", p. 29-34; Technical Developments and Instrumentation; Jan.-Feb. 1996, vol. 7, No. 1.

H.R. Andersen "History of Percutaneous Aortic Valve Prosthesis," Herz No. 34. pp. 343-346. 2009.

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

Pavonik, et al. "Development and initial Experimental Evaluation of a Prosthetic Aortic Valve for Transcatheter Placement," Cardiovascular Radiology, vol. 183, No. 1. pp. 151-154. 1992.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydro-dynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Wheatley, "Valve Prostheses," Operative Surgery, 4th ed. pp. 415-424. 1986.

* cited by examiner

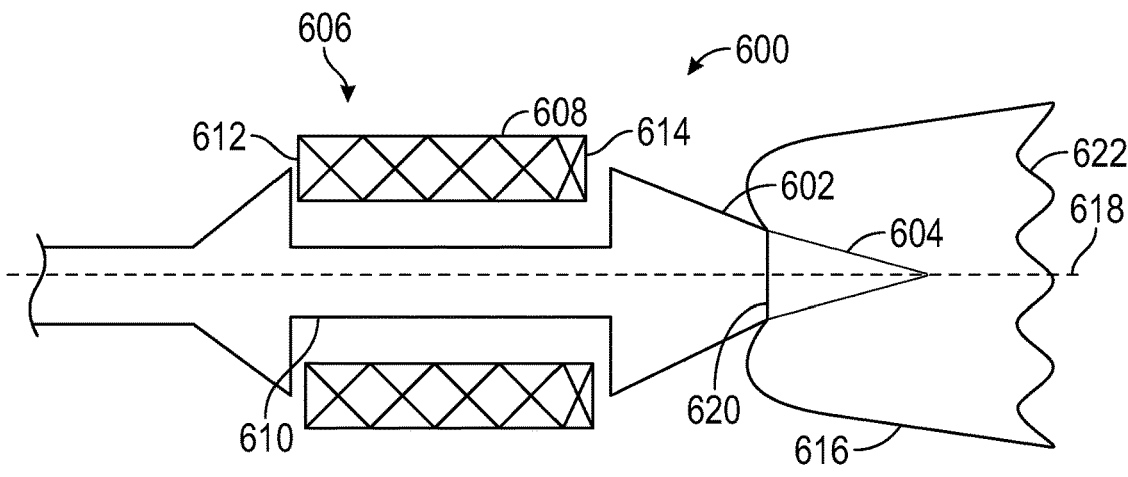
FIG. 14
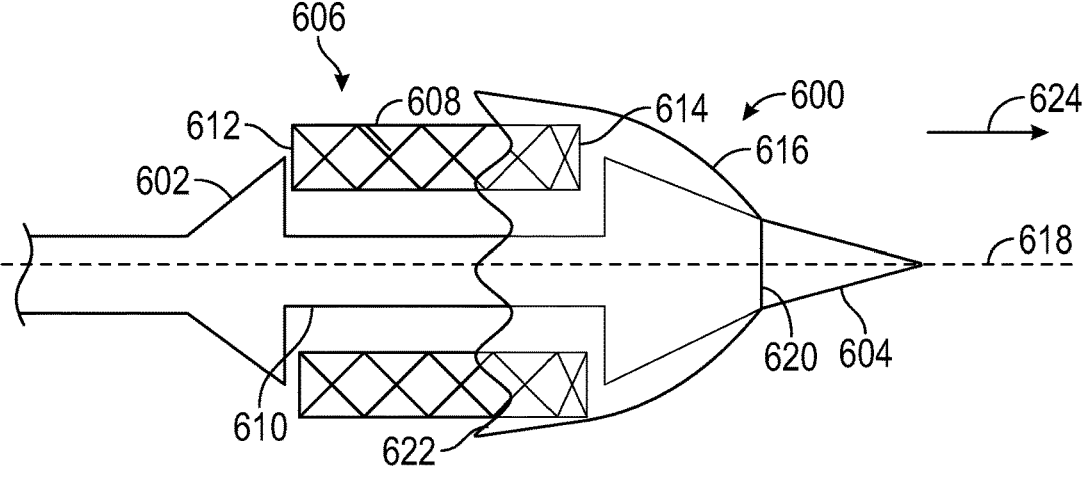
FIG. 15
FIG. 16

TRANSCATHETER HEART VALVE DELIVERY SYSTEMS AND METHODS

CROSS REFERENCE TO RELATED APPLICATION

This application is a continuation of PCT Patent Application No. PCT/US2020/044994, filed Aug. 5, 2020, which claims the benefit of U.S. Provisional Application Ser. No. 62/886,677, filed Aug. 14, 2019, all of which applications are incorporated herein by reference.

FIELD

The present disclosure concerns embodiments of systems, and related methods, for reducing contact between apices of a prosthetic medical device crimped on an end of a delivery device of a transcatheter delivery system and a delivery sheath of the transcatheter delivery system, while routing the delivery device through the delivery sheath, to a target implantation site for the prosthetic medical device, and/or reducing contact between the apices of the prosthetic medical device and the native anatomy of a patient at or along the route to the target implantation site.

BACKGROUND

Endovascular delivery devices are used in various procedures to deliver prosthetic medical devices or instruments to locations inside the body that are not readily accessible by surgery or where access without surgery is desirable. Access to a target location inside the body can be achieved by inserting and guiding the delivery device through a pathway or lumen in the body, including, but not limited to, a blood vessel, an esophagus, a trachea, any portion of the gastrointestinal tract, a lymphatic vessel, to name a few. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size such as by inflating a balloon on which the prosthetic valve is mounted, or by deploying the prosthetic valve from a sheath of the delivery device so that the prosthetic valve can self-expand to its functional size.

In some embodiments, a delivery (e.g., introducer) sheath of a transcatheter delivery system may be inserted into a patient's vasculature to aid in delivery of the prosthetic heart valve (or other prosthetic medical device, such as a stent) to the target implantation site. The path through the patient's vasculature may be tortuous, including multiple curves or bends, thereby resulting in the sheath assuming a varying and curved profile throughout its length which may include direction changes and different angles relative to an advancement direction toward the target implantation site. The prosthetic heart valve may be advanced via the delivery device, over a guidewire in some embodiments, through the sheath and the patient's vasculature to the target implantation site. The delivery device may include a nosecone arranged adjacent to a distal end of the prosthetic heart valve, at a distal end of the delivery device. The nosecone may have a tapered profile in order to assist in advancement of the prosthetic heart valve through the delivery sheath. However, the curves in the delivery sheath, along the route to the implantation site, may result in the formation of a gap between a proximal end of the nosecone and the distal end of the prosthetic heart valve. As a result of this gap formation, at least a portion of a distal end of a frame of the prosthetic heart valve may be exposed to a surrounding inner wall of the delivery sheath. In one example, apices at the distal end of the frame may contact the inner wall of the delivery sheath and result in degradation of the delivery sheath and/or the apices of the frame. In other examples, apices at the distal end of the frame may contact portions of the patient's anatomy on the way to or at the target implantation site. Accordingly, improvements in a prosthetic medical device and/or delivery device used to deliver the prosthetic medical device to a target implantation site, are desirable.

SUMMARY

Disclosed herein are prosthetic heart valves, delivery devices, nosecones for delivery devices, as well as related methods for transcatheter delivery systems and for crimping a prosthetic heart valve to a delivery device. The delivery devices can be used to deliver an implantable medical device, such as a prosthetic heart valve, to a target site in a patient, such as a heart. In some embodiments, delivery devices can be a component of a delivery system (e.g., an endovascular or transcatheter delivery system) that can be used to deliver a prosthetic heart valve or other implantable medical device. In some embodiments, the delivery system may include a delivery (e.g., introducer) sheath inserted into a lumen of a patient, such as vasculature, along a path to the target site. The delivery device may then be advanced through an interior of the sheath, to the target site.

In some embodiments, the prosthetic heart valve and/or a portion of the delivery device may be configured with one or more elements that reduce contact and/or friction between the prosthetic heart valve and the delivery sheath and/or the patient's anatomy, during maneuvering of the delivery device through the delivery sheath to the target site. As one example, distal apices of a frame of the prosthetic heart valve may be configured with a cover or cushioning element to reduce direct contact between the distal apices and inner walls of the delivery sheath. As another example, additionally or alternatively, the distal apices may be curved inward, toward a central longitudinal axis of the frame of the prosthetic hearth valve, in order to reduce direct contact between the distal apices and inner walls of the delivery sheath. As yet another example, additionally or alternatively, the nosecone of the delivery device may be configured with a jacket adapted to cover the distal apices of the frame of the prosthetic heart valve, during a valve delivery process where the valve, crimped onto the delivery device, is advanced through the delivery sheath to the target site. As another example, additionally or alternatively, the delivery device may be configured with an adjustable, proximal shoulder that is adapted to move the prosthetic valve distally, toward a distal shoulder and nosecone of the delivery device during a crimping process of the valve onto the delivery device. As a result, a gap between the distal end of the crimped valve and the distal shoulder and nosecone may be reduced, thereby reducing direct contact between the distal apices of the valve and inner walls of the delivery sheath during the valve delivery process. As yet another example, additionally or alternatively, distal apices of the frame of the prosthetic valve may have a larger width that creates an increased radius of curvature, thereby making the apices less sharp and creating a larger contact area that can reduce friction (and stress) between the apices and the sheath and/or native anatomy.

In one representative embodiment, a prosthetic heart valve can include a frame including a first end with a plurality of apices spaced apart from one another around a circumference of the first end; and a plurality of discrete cushioning elements covering the plurality of apices, wherein each cushioning element of the plurality of cushioning elements is coupled to and covers a different apex of the plurality of apices.

In some embodiments, each cushioning element comprises a flexible material folded over a corresponding apex of the plurality of apices. As one example, the flexible material comprises a fabric.

In some embodiments, each cushioning element comprises a plurality of folds arranged over and across a distal edge of a corresponding apex of the plurality of apices.

In some embodiments, for each cushioning element, the plurality of folds extends between an inner layer and an outer layer of the cushioning element. The inner layer covers an inner surface of the corresponding apex and the outer layer covers an outer surface of the corresponding apex. The inner and outer surfaces are relative to a central longitudinal axis of the prosthetic heart valve. In some embodiments, the inner layer and the outer layer are secured together around both sides of the corresponding apex. Each of the inner layer and the outer layer extend from a distal surface of the cushioning element, the distal surface formed by the plurality of folds, to a base of the corresponding apex.

In some embodiments, each cushioning element comprises an inner layer covering an inner surface of a corresponding apex of the plurality of apices, an outer layer covering an outer surface of the corresponding apex, and a distal layer defining a distal surface of the cushioning element and extending radially between the inner layer and the outer layer and across a distal edge of the corresponding apex. Each cushioning element can further include a plurality of folds arranged between the inner layer and the outer layer, and wherein each fold of the plurality of folds extends from the distal layer to a base of the corresponding apex.

In some embodiments, each cushioning element comprises one or more sutures repeatedly looped over a corresponding apex of the plurality of apices.

In some embodiments, each cushioning element comprises a pocket surrounding a corresponding apex of the plurality of apices and including a padding element disposed within the pocket, arranged distally to a distal edge of the corresponding apex.

In some embodiments, the pocket comprises a flexible material including one of a fabric and flexible polymer.

In some embodiments, overlapping folds of the pocket are secured to one another, along at least a portion of a periphery of the pocket.

In some embodiments, the pocket is fastened directly to the corresponding apex.

In some embodiments, the padding element is fixed to the pocket.

In some embodiments, the prosthetic heart valve can further include an outer skirt arranged around a circumference of the frame, at the first end, and the cushioning element is attached to the outer skirt.

In some embodiments, the prosthetic heart valve is adapted to be crimped on a delivery device with the first end arranged at a distal end of the delivery device, proximate to a nosecone of the delivery device.

In another representative embodiment, an assembly can include a delivery device including a proximal shoulder, a distal shoulder, and a nosecone arranged at distal end of the distal shoulder; and a prosthetic valve arranged in a radially compressed configuration on the delivery device, between the distal shoulder and the proximal shoulder, the prosthetic valve having a frame including a distal end arranged adjacent to the distal shoulder, the distal end of the frame having a first plurality of apices spaced apart from one another around a circumference of the distal end, wherein each apex of the first plurality of apices is curved inward toward a central longitudinal axis of the frame.

In some embodiments, the frame includes a central portion arranged between the distal end and a proximal end of the frame, the central portion being a longest portion of the frame, and the central portion is arranged parallel to the central longitudinal axis.

In some embodiments, the frame further includes a proximal end having a second plurality of apices spaced apart from one another around a circumference of the proximal end, wherein each apex of the second plurality of apices is oriented in a direction parallel to the central longitudinal axis.

In some embodiments, the frame further includes a proximal end having a second plurality of apices spaced apart from one another around a circumference of the proximal end, wherein each apex of the second plurality of apices is curved inward toward the central longitudinal axis, at an angle of curvature that is less than an angle of curvature of the first plurality of apices.

In some embodiments, the frame includes a plurality of struts, wherein the first plurality of apices is formed by meeting ends of adjacent struts of the plurality of struts, and wherein at least a portion of the adjacent struts forming the first plurality of apices are curved inward toward the central longitudinal axis.

In some embodiments, the assembly can further include an outer skirt arranged around a circumference of the frame, at the distal end of the frame, on an outside of the frame.

In some embodiments, a diameter of the frame, at the distal end of the frame, is smaller than a diameter of the frame at a proximal end of the frame and the same or smaller than a proximal end of the nosecone.

In some embodiments, each apex of the first plurality of apices is curved inward at an angle, relative to a line parallel with the central longitudinal axis and the angle is less than 45 degrees.

In some embodiments, a first end of a jacket is attached to a proximal end of the nosecone and a free, second end of the jacket is adapted to translate between positions that are proximal and distal to the first end. In some embodiments, the jacket comprises one or more of a fabric, tissue, and a polymeric sheet.

In some embodiments, the assembly can further include a bio-resorbable element covering the first plurality of apices at the distal end of the frame of the prosthetic valve.

In some embodiments, the distal shoulder and the proximal shoulder are mounted to a shaft of the delivery device. The proximal shoulder is radially crimpable and mounted to the shaft at a location proximal to the distal shoulder, the proximal shoulder including an outer surface adapted to interface with a valve crimper and a distal edge adapted to move axially toward the distal shoulder, relative to a central longitudinal axis of the shaft, when a crimping force is applied to the outer surface to move the proximal shoulder from an uncrimped state to a crimped state. The proximal shoulder is plastically deformable such that the proximal shoulder remains in the crimped state after crimping.

In another representative embodiment, a nosecone for a delivery device can include a nosecone body; and a jacket including a first end attached to the nosecone body and a free, second end adapted to translate between positions that are proximal and distal to the first end.

In some embodiments, the first end of the jacket is attached to a proximal end of the nosecone body, the proximal end adapted to be coupled to a distal shoulder of the delivery device.

In some embodiments, the second end is unattached to the nosecone body along an entire edge of the second end.

In some embodiments, the jacket comprises one or more of a fabric, tissue, and a polymeric sheet.

In some embodiments, the jacket is translatable between a proximal, first position wherein the second end is arranged over a distal end of a frame of a prosthetic valve crimped onto a balloon of the delivery device and a distal, second position wherein the second end is arranged distally away from the distal end of the frame.

In some embodiments, the jacket is in the first position during delivery of a prosthetic valve crimped onto the balloon, where the delivery device is advanced through a delivery sheath to a target implantation site for the prosthetic valve and the jacket is in the second position after inflation of the balloon and deployment of the prosthetic valve.

In another representative embodiment, a method for a transcatheter delivery system can include inserting a distal end portion of a delivery device and a prosthetic valve into vasculature of a patient, wherein the prosthetic valve is in a crimped (e.g., radially compressed) state around a balloon of the delivery device at a location proximal to a nosecone of the delivery device with a nosecone jacket covering a distal end of a frame of the prosthetic valve; and inflating the balloon to radially expand the prosthetic valve, which causes the nosecone jacket to slide off of the distal end of the frame, in a distal direction.

In some embodiments, the distal end of the prosthetic valve includes a plurality of apices arranged around a circumference of the distal end and the distal end of the prosthetic valve is oriented proximate to the nosecone.

In some embodiments, inserting the distal end portion of the delivery device into the vasculature of the patient includes inserting the distal end portion of the delivery device, including the prosthetic valve, into and through an introducer sheath inserted into the vasculature of the patient. The method can further include maintaining the nosecone jacket covering the distal end of the frame of the prosthetic valve during advancing the distal end portion of the delivery device through the introducer sheath and the vasculature of the patient to a target implantation site for the prosthetic valve.

In some embodiments, when the nosecone jacket covers the distal end of the frame, the nosecone jacket coverts the plurality of apices of the distal end and provides a barrier between the plurality of apices and the introducer sheath.

In some embodiments, the nosecone jacket is attached at a first, fixed end to the nosecone and includes a second, free end and the method can further include, prior to crimping the prosthetic valve around the balloon of the delivery device, orienting the free end of the nosecone jacket distally away from the frame of the prosthetic valve, relative to a central longitudinal axis of the delivery device.

In some embodiments, the nosecone jacket comprises a material including one or more of fabric, tissue, and a polymeric sheet that is adapted to translate freely between positions where a free end of the nosecone jacket covers the distal end of the frame and slides off the distal end of the frame.

In another representative embodiment, a prosthetic heart valve can include a frame including a proximal end and a distal end including a plurality of apices; and a bio-resorbable element covering the plurality of apices at the distal end.

In some embodiments, the bio-resorbable element is a dissolving biofilm.

In some embodiments, the bio-resorbable element is a bio-resorbable polymer.

In some embodiments, the bio-resorbable element is wrapped around an entire circumference of the distal end of the frame.

In some embodiments, the bio-resorbable element is wrapped around a circumference of the distal end of the frame in a single layer.

In some embodiments, the bio-resorbable element is wrapped around a circumference of the distal end of the frame in multiple layers.

In some embodiments, the bio-resorbable element is adapted to degrade in a pre-determined time frame that is based on a time to advance the prosthetic heart valve, crimped on a delivery device, through a sheath to a desired implantation site in a patient.

In some embodiments, each apex of the plurality of apices is curved inward toward a central longitudinal axis of the frame.

In another representative embodiment, a delivery device for a transcatheter delivery system can include a shaft; a distal shoulder mounted to the shaft; and a radially crimpable proximal shoulder spaced apart from the distal shoulder and mounted to the shaft at a location proximal to the distal shoulder, the proximal shoulder including an outer surface adapted to interface with a valve crimper and a distal edge adapted to move axially toward the distal shoulder, relative to a central longitudinal axis of the shaft, when a crimping force is applied to the outer surface to move the proximal shoulder from an uncrimped state to a crimped state; wherein the proximal shoulder is plastically deformable such that the proximal shoulder remains in the crimped state after crimping.

In some embodiments, the delivery device can further include a balloon arranged around the shaft, distal shoulder, and proximal shoulder.

In some embodiments, a prosthetic valve is adapted to be crimped around the balloon, in a space arranged between the distal shoulder and the proximal shoulder.

In some embodiments, the distal edge is a circumferential edge arranged perpendicular to an outer surface of the shaft and the outer surface is a circumferential surface arranged concentric with and parallel to the outer surface of the shaft.

In some embodiments, the proximal shoulder includes an inclined edge arranged between a proximal edge of the proximal shoulder and the distal edge that is angled relative to the central longitudinal axis and the inclined edge is adapted to pivot towards the shaft and about the proximal edge.

In another representative embodiment, a method for crimping a prosthetic valve to a delivery device can include arranging a prosthetic valve on a valve-mounting portion of a balloon, between a distal shoulder and proximal shoulder mounted on a shaft of the delivery device, the proximal shoulder and distal shoulder arranged within the balloon; and crimping the prosthetic valve onto the balloon via exerting an inward, radial force, relative to a central longitudinal axis of the valve shaft, against the prosthetic valve and an outer surface of the proximal shoulder, wherein the inward, radial force causes a distal edge of the proximal shoulder to move axially toward the prosthetic valve and the distal shoulder and exert an axial push force on a proximal end of the frame of the prosthetic valve, moving the prosthetic valve distally toward the distal shoulder while the prosthetic valve is radially compressed.

In some embodiments, the outer surface is spaced farther away from the shaft prior to crimping than after crimping.

In some embodiments, the distal edge is a circumferential edge extending around a circumference of the shaft and arranged perpendicular to an outer surface of the shaft and the distal edge is spaced farther away from the proximal end of the frame prior to crimping than after crimping.

In some embodiments, the proximal shoulder includes an inclined edge arranged between a proximal edge of the proximal shoulder and the distal edge of the proximal shoulder and angled relative to the central longitudinal axis of the shaft and the inclined edge pivots about the proximal edge as the inward, radial force is exerted on the outer surface of the proximal shoulder, moving the inclined edge closer to the valve shaft and decreasing an angle between the inclined edge and the proximal edge.

In some embodiments, the proximal shoulder is plastically deformable about the proximal edge and, after crimping, the proximal shoulder maintains its position, including the decreased angle between the inclined edge and the proximal edge and the distal edge abutting the proximal end of the frame.

The foregoing and other objects, features, and advantages of the invention will become more apparent from the following detailed description, which proceeds with reference to the accompanying figures.

BRIEF DESCRIPTION OF THE DRAWINGS

FIG. 14 is a schematic showing a prosthetic valve in a crimped (e.g., radially compressed) state on a delivery device of a delivery system, prior to insertion of the delivery device into a delivery sheath of the delivery system.

FIG. 15 is a schematic showing the prosthetic valve in a crimped state on the delivery device of FIG. 14, during valve delivery through the delivery sheath of the delivery system.

FIG. 16 is a schematic showing the prosthetic valve in an expanded state after inflation of a balloon of the delivery device of FIG. 14, after reaching a target implantation site.

DETAILED DESCRIPTION

Described herein are examples of prosthetic heart valves, delivery devices configured to deliver prosthetic heart valves to target implantation locations within a body, and/or components of delivery devices and methods for transcatheter delivery systems and for crimping a prosthetic heart valve to a delivery device. The prosthetic heart valves may include a frame including a proximal end and distal end, the distal end including a plurality of apices arranged around a circumference of the distal end. As used herein, the "distal end" of the frame may refer to the end of the frame that is positioned proximate and/or adjacent to a distal shoulder/nosecone of a delivery device when crimped around a valve retaining portion of the delivery device. For example, the distal end may be oriented further downstream than the proximal end of the frame when the delivery device to which the valve is crimped is being advanced through a lumen of a patient, toward a target implantation site.

The delivery device, which may include a balloon shoulder assembly including a proximal and/or distal shoulder, a nosecone arranged at a distal end of the delivery device, and a balloon, may be inserted into a delivery sheath of the delivery device, inserted into a lumen (e.g., blood vessel) of a patient, and advanced through the delivery sheath, with the prosthetic heart valve crimped thereon, to the target implantation site. In some embodiments, as described further below, the prosthetic heart valve and/or portions of the delivery device may be configured with one or more elements that reduce the likelihood of direct contact between distal apices of the valve frame and inner walls of the delivery sheath, during advancement of the delivery device to the target implantation site. In some embodiments, the prosthetic heart valve may be additionally or alternatively configured to reduce friction between distal apices of a frame of the prosthetic heart valve and the delivery sheath, during advancement of the delivery device and prosthetic heart valve to the target implantation site. As a result, degradation of the sheath and/or valve may be reduced during a valve delivery process and the delivery device may be more easily maneuvered (e.g., with less resistance) to the target implantation site.

Figure 1:
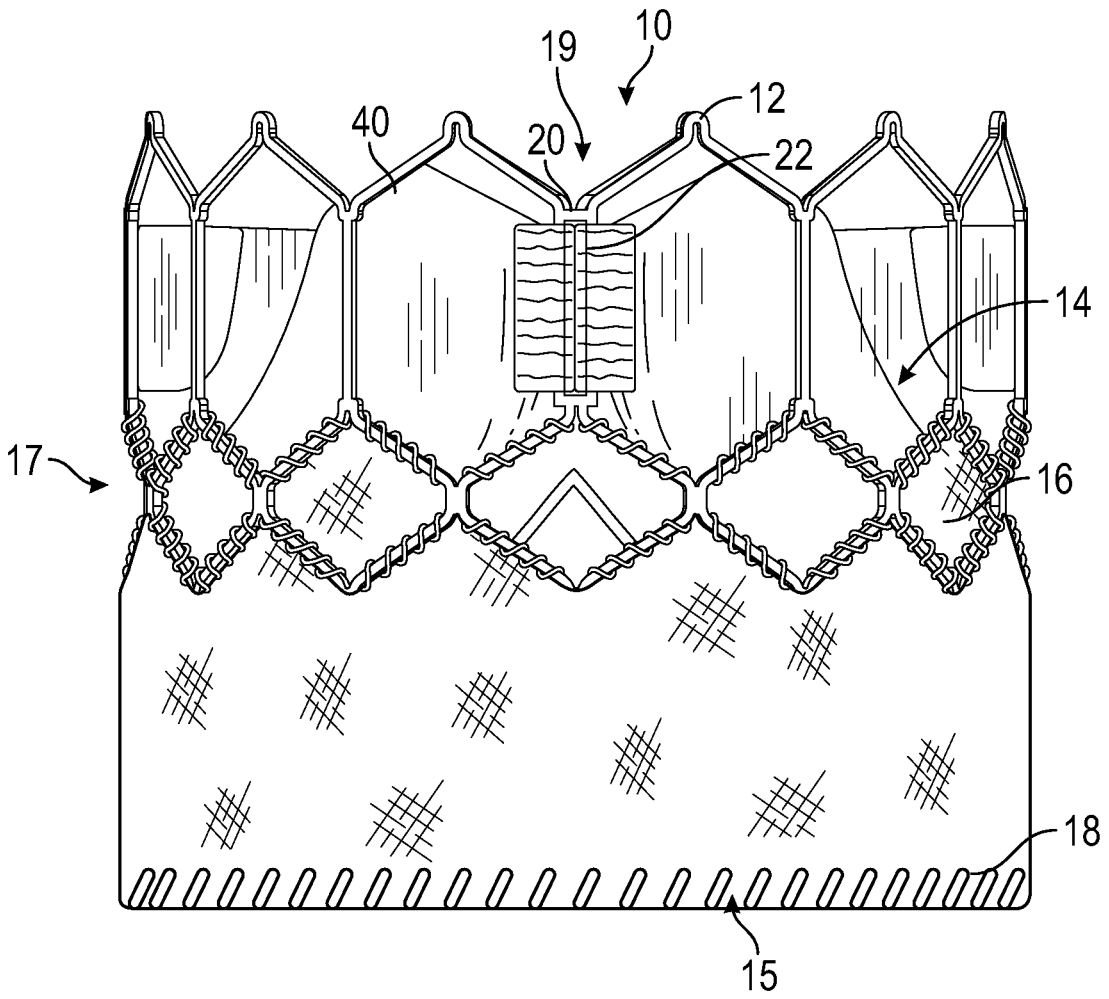
FIG. 1 is a perspective view of a prosthetic heart valve, according to one embodiment.

FIG. 1 shows a prosthetic heart valve 10, according to one embodiment. The illustrated prosthetic valve is adapted to be implanted in the native aortic annulus, although in other embodiments it can be adapted to be implanted in the other native annuluses of the heart (e.g., the pulmonary, mitral, and tricuspid valves). The prosthetic valve can also be adapted to be implanted in other tubular organs or passageways in the body. The prosthetic valve 10 can have four main components: a stent or frame 12, a valvular structure 14, an inner skirt 16, and a perivalvular outer sealing member or outer skirt 18. The prosthetic valve 10 can have an inflow end portion 15, an intermediate portion 17, and an outflow end portion 19.

The valvular structure 14 can comprise three leaflets 40, collectively forming a leaflet structure, which can be arranged to collapse in a tricuspid arrangement, although in other embodiments there can be greater or fewer number of leaflets (e.g., one or more leaflets 40). The leaflets 40 can be secured to one another at their adjacent sides to form commissures 22 of the leaflet structure 14. The lower edge of valvular structure 14 can have an undulating, curved scalloped shape and can be secured to the inner skirt 16 by sutures (not shown). In some embodiments, the leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The frame 12 can be formed with a plurality of circumferentially spaced slots, or commissure windows 20 that are adapted to mount the commissures 22 of the valvular structure 14 to the frame. The frame 12 can be made of any of various suitable plastically-expandable materials (e.g., stainless steel, etc.) or self-expanding materials (e.g., nickel titanium alloy (NiTi), such as nitinol), as known in the art. When constructed of a plastically-expandable material, the frame 12 (and thus the prosthetic valve 10) can be crimped to a radially collapsed configuration on a delivery catheter and then expanded inside a patient by an inflatable balloon or equivalent expansion mechanism. When constructed of a self-expandable material, the frame 12 (and thus the prosthetic valve 10) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size.

Suitable plastically-expandable materials that can be used to form the frame 12 include, without limitation, stainless steel, a biocompatible, high-strength alloys (e.g., a cobalt-chromium or a nickel-cobalt-chromium alloys), polymers, or combinations thereof. In particular embodiments, frame 12 is made of a nickel-cobalt-chromium-molybdenum alloy, such as MP35N® alloy (SPS Technologies, Jenkintown, Pa.), which is equivalent to UNS R30035 alloy (covered by ASTM F562-02). MP35N® alloy/UNS R30035 alloy comprises 35% nickel, 35% cobalt, 20% chromium, and 10% molybdenum, by weight. Additional details regarding the prosthetic valve 10 and its various components are described in WIPO Patent Application Publication No. WO 2018/222799, which is incorporated herein by reference.

Figures 2A, 2B:
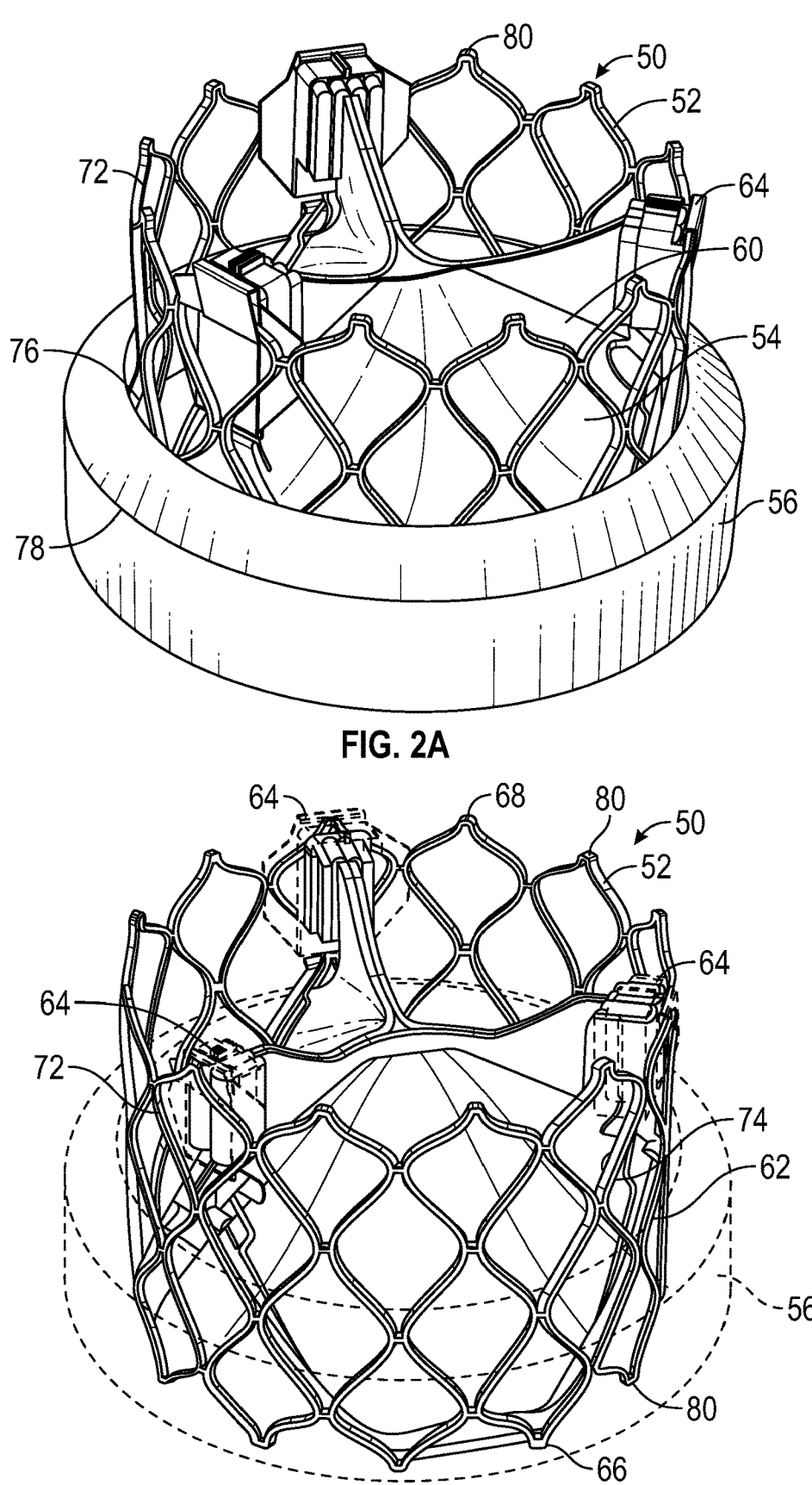
FIG. 2A is a perspective view of a prosthetic heart valve, according to another embodiment.
FIG. 2B is a perspective view of the prosthetic valve of FIG. 2A with the components on the outside of the frame shown in transparent lines for purpose of illustration.

FIG. 2A is a perspective view of a prosthetic heart valve 50, according to another embodiment. The valve 50 can have three main components: a stent or frame, 52, a valvular structure 54, and a sealing member 56. FIG. 2B is a perspective view of the prosthetic valve 50 with the components on the outside of the frame 52 (including the sealing member 56) shown in transparent lines for purposes of illustration.

Like the valvular structure 14 of FIG. 1, the valvular structure 54 can comprise three leaflets 60, collectively forming a leaflet structure, which can be arranged to collapse in a tricuspid arrangement. Each leaflet 60 can be coupled to the frame 52 along its inflow edge 62 (the lower edge in the figures; also referred to as "cusp edges") and at commissures 64 of the valvular structure 54 where adjacent portions of two leaflets are connected to each other. A reinforcing element (not shown), such as a fabric strip, can be connected directly to the cusp edges of the leaflets and to the struts of the frame to couple the cusp edges of the leaflets to the frame.

Similar to the frame 12 of FIG. 1, the frame 52 can be made of any of various suitable plastically-expandable materials or self-expanding materials, as known in the art and described above. The frame 52 in the illustrated embodiment comprises a plurality of circumferentially extending rows of angled struts 72 defining rows of cells, or openings, 74 of the frame. The frame 52 can have a cylindrical or substantially cylindrical shape having a constant diameter from an inflow end 66 to an outflow end 68 of the frame as shown, or the frame can vary in diameter along the height of the frame, as disclosed in U.S. Patent Publication No. 2012/0239142, which is incorporated herein by reference.

The frame 52, at each of the inflow end 66 and the outflow end 68, may comprise a plurality of apices 80 spaced apart from one another around a circumference of the frame 52.

The sealing member 56 in the illustrated embodiment is mounted on the outside of the frame 52 and functions to create a seal against the surrounding tissue (e.g., the native leaflets and/or native annulus) to prevent or at least minimize paravalvular leakage. The sealing member 56 can comprise an inner layer 76 (which can be in contact with the outer surface of the frame 52) and an outer layer 78. The sealing member 56 can be connected to the frame 52 using suitable techniques or mechanisms. For example, the sealing member 56 can be sutured to the frame 52 via sutures that can extend around the struts 72 and through the inner layer 76. In alternative embodiments, the inner layer 76 can be mounted on the inner surface of the frame 52, while the outer layer 78 is on the outside of the frame 52.

The outer layer 78 can be configured or shaped to extend radially outward from the inner layer 76 and the frame 52 when the prosthetic valve 50 is deployed. When the prosthetic valve is fully expanded outside of a patient's body, the outer layer 78 can expand away from the inner layer 76 to create a space between the two layers. Thus, when implanted inside the body, this allows the outer layer 78 to expand into contact with the surrounding tissue.

Additional details regarding the prosthetic valve 50 and its various components are described in U.S. Patent Publication No. 2018/0028310, which is incorporated herein by reference.

Figure 3:
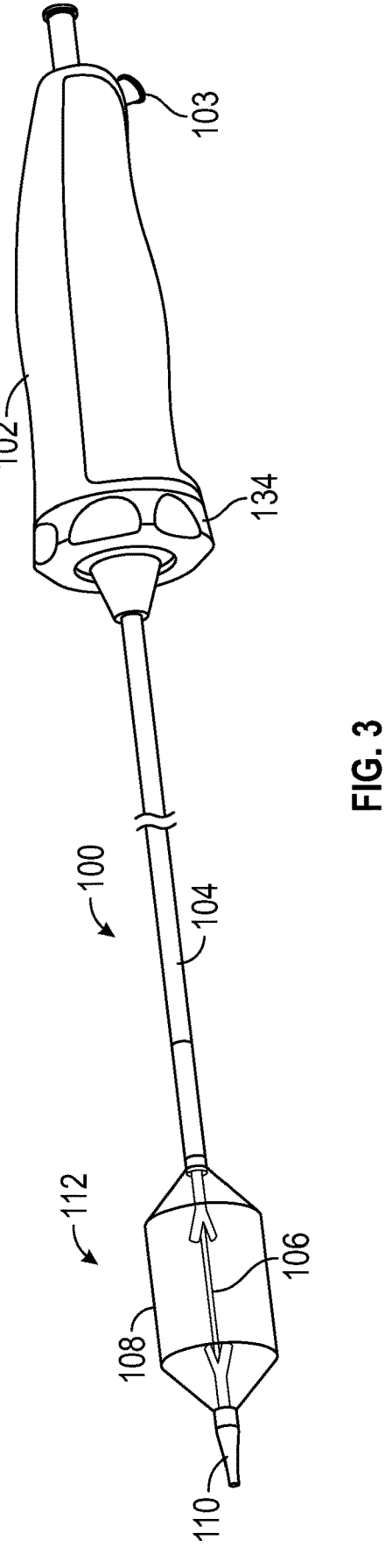
FIG. 3 is a perspective view of a delivery device for a prosthetic heart valve, according to an embodiment.
Figures 4, 5, 6:
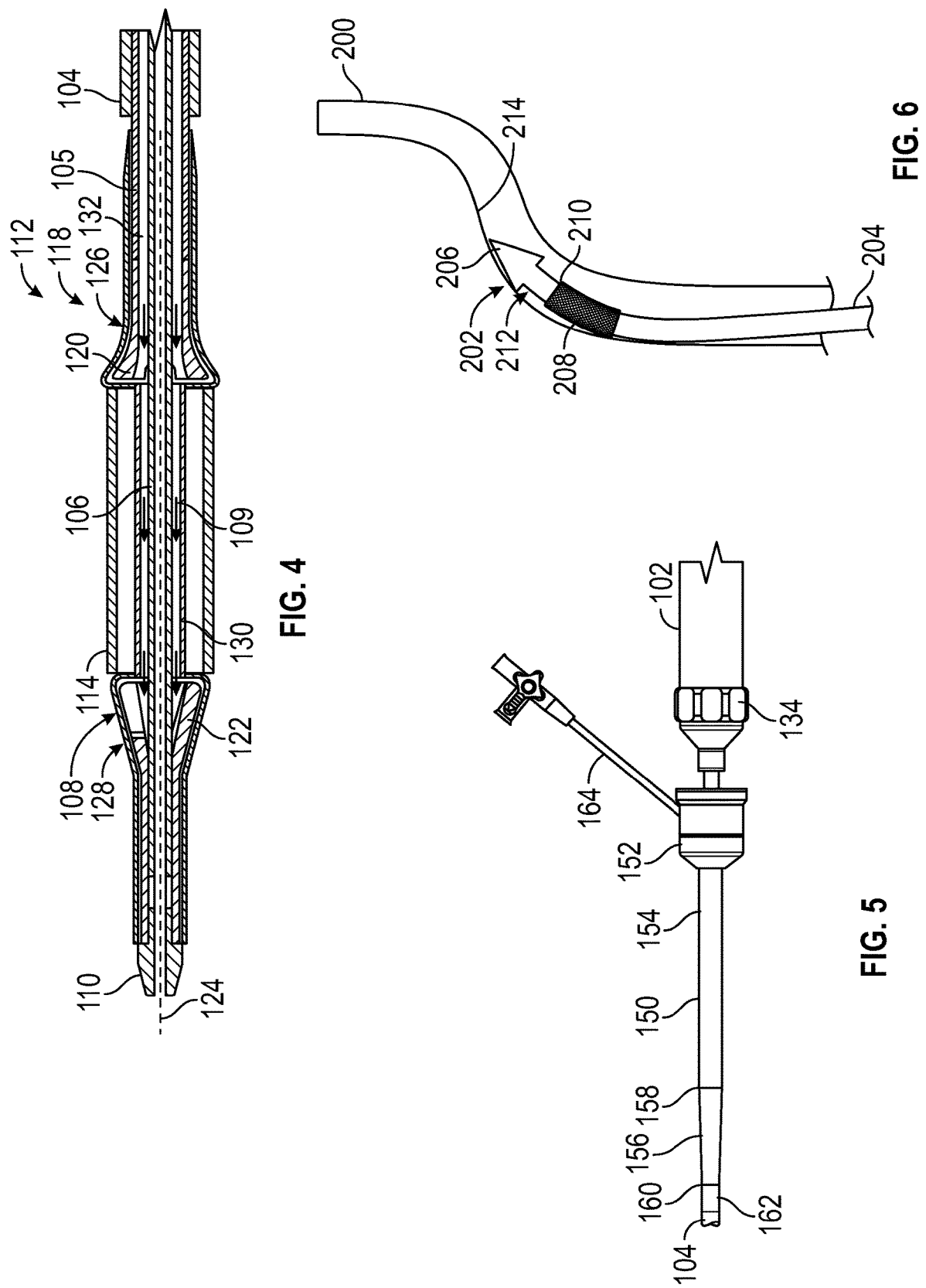
FIG. 4 is a cross-sectional view of an embodiment of a distal end portion of the delivery device of FIG. 3.
FIG. 5 is a side view of an introducer sheath, according to an embodiment, which may be used in a delivery system to introduce the delivery device of FIG. 3 into a body of a patient.
FIG. 6 is a schematic of an exemplary delivery sheath arranged within a patient's blood vessel and an exemplary delivery device being advanced through the delivery sheath.

FIGS. 3-5 show various components of a delivery system, such as a transcatheter delivery system, including a delivery device and an introducer sheath (also referred to herein as a delivery sheath). FIG. 3 shows a delivery device (e.g., apparatus) 100, according to an embodiment, that can be used to implant an expandable prosthetic heart valve (e.g., heart valve 10 or 50), or another type of expandable prosthetic medical device (such as a stent). In some embodiments, the delivery device 100 is specifically adapted for use in introducing a prosthetic valve into a heart. A delivery system for implanting a prosthetic heart valve can comprise the delivery device 100 and an introducer (e.g., delivery) sheath 150 (shown in FIG. 5).

Referring to FIG. 3, the delivery device 100 in the illustrated embodiment is a balloon catheter comprising a handle 102, a steerable, outer shaft 104 extending from the handle 102, an intermediate shaft 105 (see FIG. 4) extending from the handle 102 coaxially through the steerable outer shaft 104, and an inner shaft 106 extending from the handle 102 coaxially through the intermediate shaft 105 and the steerable shaft 104, an inflatable balloon 108 extending from a distal end of the intermediate shaft 105, and a nosecone 110 arranged at a distal end of the delivery device 100. A distal end portion 112 of the delivery device 100 includes the balloon 108, the nosecone 110, and a balloon shoulder assembly. A prosthetic medical device, such as a prosthetic heart valve may be mounted on a valve retaining portion of the balloon 108, as described further below with reference to FIG. 4. As described further below, the balloon shoulder assembly is configured to maintain the prosthetic heart valve or other medical device at a fixed position on the balloon 108 during delivery through the patient's vasculature.

The handle 102 can include a steering mechanism configured to adjust the curvature of the distal end portion of the delivery device. In the illustrated embodiment, for example, the handle 102 includes an adjustment member, such as the illustrated rotatable knob 134, which in turn is operatively coupled to the proximal end portion of a pull wire (not shown). The pull wire extends distally from the handle 102 through the outer shaft 104 and has a distal end portion affixed to the outer shaft at or near the distal end of the outer shaft 104. Rotating the knob 134 is effective to increase or decrease the tension in the pull wire, thereby adjusting the curvature of the distal end portion of the delivery device.

FIG. 4 shows an embodiment of the distal end portion 112 of the delivery device 100. As shown in FIG. 4, the delivery device 100 is configured to mount a prosthetic valve (e.g., prosthetic heart valve) 114 in a crimped (e.g., radially compressed) state over the balloon 108 for insertion of the delivery device 100 and prosthetic valve 114 into a patient's vasculature.

As shown in FIG. 4, at a proximal end of the distal end portion 112, the inner shaft 106 extends distally beyond the steerable shaft 104 and the intermediate shaft 105 and through the balloon 108. The balloon 108 can be supported on a balloon shoulder assembly 118. The balloon shoulder assembly 118 includes a proximal shoulder 120 connected to a distal end of the intermediate shaft 105 and a distal shoulder 122 mounted on the inner shaft 106. The balloon 108 includes a proximal end portion 126 surrounding and/or folded over the proximal shoulder 120 and a distal end portion 128 surrounding and/or folded over the distal shoulder 122. In some embodiments, the proximal end portion 126 of the balloon 108 may be secured to the outer surface of the intermediate shaft 105. In some embodiments, the distal end portion 128 of the balloon 108 may be secured to the outer surface of the nosecone 110, which can be mounted on or coupled to the inner shaft 106.

In the illustrated embodiment, the nosecone 110 and the distal shoulder 122 can be a one-piece or unitary component, that is, the nosecone 110 is a distal portion of the unitary component and the distal shoulder 122 is a proximal portion of the unitary component. In other embodiments, the nosecone 110 and the distal shoulder 122 can be separate components, and each can be mounted on the inner shaft 106 next to each other or at axially spaced locations.

The proximal shoulder 120 and the distal shoulder 122 are spaced apart from one another, in an axial direction relative to a central longitudinal axis 124 of the delivery device 100. As a result, the balloon 108 defines a valve-retaining portion in the space that separates the proximal shoulder 120 and the distal shoulder 122 (e.g., between flared ends of the proximal shoulder 120 and the distal shoulder 122). As shown in FIG. 4, the prosthetic valve 114 can be crimped onto the valve retaining portion 130 of the balloon 108, between the proximal shoulder 120 and the distal shoulder 122, thereby preventing or reducing axial movement of the prosthetic valve 114 relative to the balloon 108 during insertion of the delivery device 100 into the patient and delivery of the prosthetic valve 114 to the target implantation site.

The outer diameter of the inner shaft 106 can be sized such that an annular space 132 is defined between the inner shaft 106 and the intermediate shaft 105 along the entire length of the intermediate shaft 105. The annular space 132 may be fluidly coupled to one or more fluid passageways of the delivery device 100 which can be fluidly connectable to a fluid source (e.g., a syringe) that can inject an inflation fluid (e.g., saline) into the delivery device. In this way, fluid from the fluid source can flow through the one or more fluid passageways, through the annular space 132, and into the balloon 108 to inflate the balloon 108 and expand and deploy the prosthetic valve 114. For example, the handle 102 can have a fluid port 103 (see FIG. 3) configured to be coupled to the fluid source. In use, inflation fluid from the fluid source can be injected into the fluid port 103, through one or more fluid passageways in the handle 102, through the annular space 132, and into the balloon 108.

FIG. 4 illustrates the flow of fluid (indicated by arrows 109) through the annular space 132 and through passages in the proximal shoulder 120 and distal shoulder 122. The fluid can then flow into the proximal and distal end portions 126, 128 of the balloon 108 to expand the valve 114. Further details of the balloon shoulder assembly, the steering mechanism, and other components of the delivery device are disclosed in U.S. Publication Nos. 2007/0005131, 2009/0281619, 2013/0030519, and 2017/0065415, which are incorporated herein by reference.

FIG. 5 shows an embodiment of an introducer (e.g., delivery) sheath 150 which may be used in the delivery system to introduce the delivery device 100 into the body of a patient. The introducer sheath 150 in the illustrated embodiment includes an introducer housing (also referred to herein as a "hub") 152 and an introducer sleeve 154 extending from the housing 152. The housing 152 houses one or more valves. In one embodiment, the one or more valves may include a sealing valve. A protruding component 164, which may be a stopcock, as shown in FIG. 5, extends outward and away from the housing 152.

In use, the sleeve 154 is inserted into a body vessel (e.g., the femoral artery) while the housing 152 remains outside the body. The delivery device 100 is inserted through a proximal opening in the housing 152, the one or more valves within the housing 152, the sleeve 154, and into the body vessel. The one or more valves of the housing 152 may sealingly engage the outer surface of the steerable shaft 104 to minimize blood loss. In some applications, a loader device (not shown) can be placed over the distal end portion of the delivery device and the prosthetic valve before the distal end portion of the delivery device and the prosthetic valve are inserted into the housing 152. The loader device prevents the one or more valves inside the housing 152 from directly contacting the prosthetic valve as it is pushed through the introducer sheath.

The sleeve 154 can have a tapered section 156 that tapers from a first diameter at a proximal end 158 to a second, smaller diameter at a distal end 160. A reduced diameter distal end portion 162 extends from the tapered portion 156 to the distal end of the sleeve 154. The tapered portion 156 provides for a smoother transition between the outer surface of the sleeve 154 and the outer surface of the steerable shaft 104. The tapered portion 156 also allows for variable placement of the sleeve 154 in the patient's vasculature to help minimize complete occlusion of the femoral artery. In some embodiments, the sleeve 154 can be configured to locally expand as the prosthetic valve is advanced through the sleeve. Further details regarding the introducer sheath are disclosed in U.S. Publication No. 2016/0296730, which is incorporated herein by reference.

While FIG. 5 shows one example embodiment of an introducer sheath 150, in alternate embodiments, the transcatheter delivery system, including delivery device 100, may be used with an introducer sheath having a different configuration (e.g., such as a different overall shape, different components, and the like). Further, in alternate embodiments, the delivery device 100 may include additional or different components than those shown in FIGS. 3-5. As such, FIGS. 3-5 shows one example embodiment of a (transcatheter) delivery system that may be used to deliver a prosthetic heart valve to a target implantation site.

FIG. 6 depicts a schematic example of a delivery (e.g., introducer) sheath 200 arranged within a patient's blood vessel. The sheath 200 may extend along a portion of a length of the patient's blood vessel, in route to a target implantation site. As shown in FIG. 6, the sheath 200 may have one or more bends 202 along its length, due to a curved nature of the patient's blood vessel in which it is inserted. For example, the sheath 200 may assume a curved profile throughout its length, including multiple curves or bends having different angles that are oriented at different directions, based on an architecture of the patient's vasculature.

As shown in FIG. 6, a delivery device 204 is inserted into the sheath 200 and routed through an inside of the sheath 200, toward the target implantation site. In some embodiments, the delivery device 204 may be similar to the delivery device 100 depicted in FIGS. 3-5, as described above. The delivery device 204 includes a distal end portion with a tapered nosecone 206 and a prosthetic valve 208 crimped onto the distal end portion, upstream of and adjacent to the nosecone 206. A distal end 210 of the prosthetic valve 208 is arranged adjacent to a proximal end of the nosecone 206 and may include a metal frame having a plurality of apices arranged around a circumference of the distal end 210. In some embodiments, the prosthetic valve 208 may be one of the valves shown in FIGS. 1-2B, as described above.

As introduced above, the bends (or curves) in the sheath 200, such as bend 202, within the patient's vasculature may cause the delivery device 204 to curve as it is advanced through the sheath 200. As shown in FIG. 6, as the delivery device 204 is routed through the bend 202, a gap 212 can be formed between the proximal end of the nosecone 206 and the distal end 210 of the prosthetic valve 208. The size of the gap in the drawing is exaggerated for purposes of illustration. As a result of the formation of the gap 212, a portion of the distal end 210 of the frame of the prosthetic valve 208 may be exposed to the surrounding inner wall 214 of the sheath 200. For example, apices of the frame of the prosthetic valve 208, at the distal end 210, may be exposed to and come into contact with the inner wall 214 of the sheath 200, as the delivery device 204 is navigated through the bend 202. Direct contact between the apices of the distal end 210 of the frame and the sheath 200 may cause degradation of the sheath 200 and/or the apices of the prosthetic valve 202. In some embodiments, if the apices of the frame of the prosthetic valve 208 are pressed against the inner wall 214 with a great enough force at specific angles, the apices may puncture the inner wall 214 of the sheath 200.

Further, in some embodiments, apices of the frame of the prosthetic valve 208 may come into contact with the native anatomy of the patient, either along the delivery route to or at the target implantation site.

For example, in some embodiments, contact of the relatively stiff apices of the frame of the prosthetic valve 208 with the softer (e.g., less stiff) sheath 200 may result in increased friction between the two surfaces (valve apices and inner wall of the sheath), thereby resulting in adherence between the apices and the sheath (making it more difficult to advance the valve through the sheath the target implantation site) and potential damage to the sheath. Additionally, due to a relatively small contact area of the apices (e.g., creating relatively sharp apices) against the sheath, the sheath may become degraded or damaged during contact with the apices of the frame.

Thus, it is desirable to provide prosthetic valve and/or delivery device configurations that decrease a likelihood of causing degradation to the delivery sheath and/or the valve during delivery of the device to a target implantation site, via the delivery device (referred to herein as a valve delivery process). Additionally, or alternatively, it may be desirable to provide prosthetic valve and/or delivery device configurations that decrease a likelihood of contact between apices of the prosthetic valve and the delivery sheath and/or a patient's anatomy. Additionally, or alternatively, it may be desirable to provide prosthetic valve and/or delivery device configurations that decrease a coefficient of friction and stress between the apices of the prosthetic valve and the delivery sheath and/or a patient's anatomy.

In one embodiment, one or more cushioning elements may be adapted to cover apices arranged at a distal end of a frame of a prosthetic valve, in order to mitigate a likelihood of abrasion of inner walls of the delivery sheath with the prosthetic valve. FIGS. 7-11 show embodiments of cushioning elements for apices arranged at the distal end of the frame of the prosthetic valve.

Figures 7, 8:
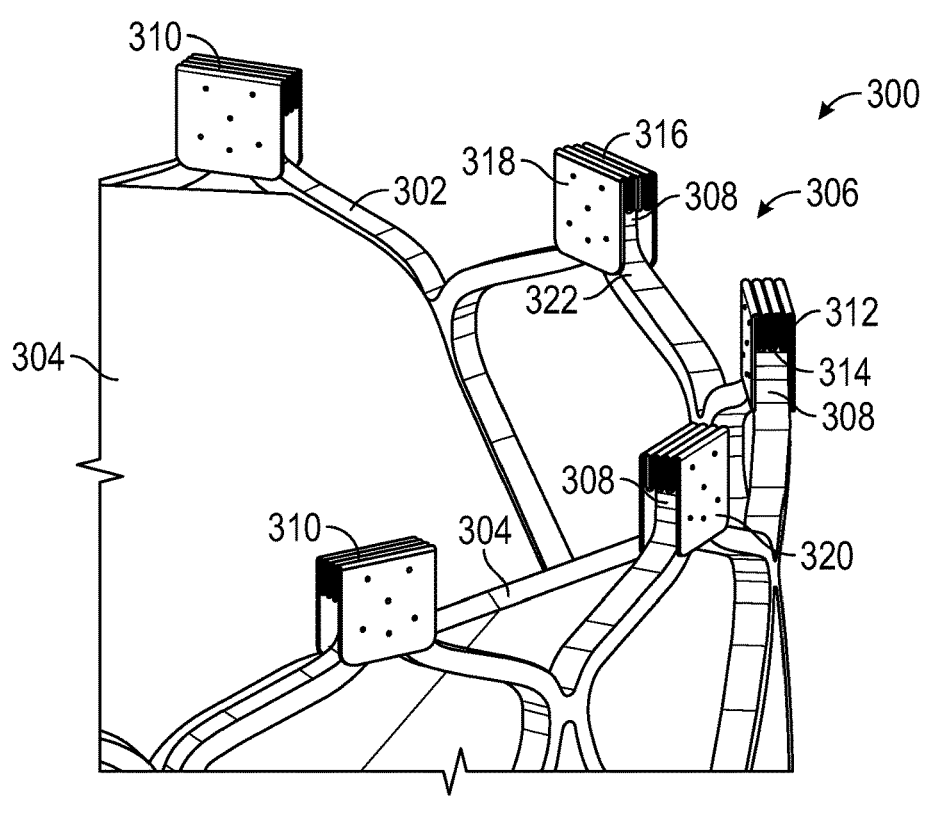
FIG. 7 is a partial view of a prosthetic valve including a plurality of apices covered by a cushioning element, according to a first embodiment.
FIG. 8 is a partial view of the prosthetic valve showing a single apex of the valve covered by a cushioning element, according to a second embodiment.

Turning first to FIG. 7, a partial view of a prosthetic valve including a plurality of apices covered by a cushioning element, according to a first embodiment, is shown. Specifically, FIG. 7 shows a prosthetic heart valve (e.g., valve) 300 including a frame 302 and leaflets 304 disposed therein. In some embodiments, the valve 300 may be similar to the prosthetic heart valve 10 shown in FIG. 1 and/or the prosthetic heart valve 50 shown in FIGS. 2A-2B.

A distal (e.g., first) end 306 of the frame 302 of the valve 300 is shown in FIG. 7 and includes a plurality of apices 308 spaced apart from one another around a circumference of the distal end 306. When the valve 300 is crimped onto a delivery device, such as the delivery device 100 shown in FIGS. 3-5 and/or the delivery device 204 shown in FIG. 6, the distal end 306 of the frame 302 may be arranged adjacent to a proximal end of a distal shoulder and/or nosecone of the delivery device. An opposite, proximal end of the frame 302 (not shown in FIG. 7) may then be arranged adjacent to a proximal shoulder of the delivery device and farther away from the nosecone than the distal end 306.

In some embodiments, as shown in FIG. 7, each apex 308 of the plurality of apices includes a discrete cushioning element 310 covering at least a distal end of the apex 308. In alternate embodiments, a single cushioning element may cover each and every apex of the plurality of apices 308 of the valve 300. For example, in these embodiments, the single cushioning element may comprise a single, circumferential sleeve, arranged around an entirety of the circumference of the distal end 306 and covering all of the plurality of apices 308. In other embodiments, the valve 300 may include two or more cushioning elements, each covering at least two apices 308. In still other embodiments, the cushioning element or elements may be part of an external skirt (e.g., skirt 18) or an internal skirt (e.g., skirt 16) of the valve 300. In these embodiments, the skirt may have integral individual cushioning elements or a single cushioning element.

As shown in FIG. 7, each cushioning element 310 is coupled to and covers, at least a portion (e.g., a distal end) of a different apex 308 of the plurality of apices. Each cushioning element 310 may comprise a flexible material folded over an apex 308. In some embodiments, the flexible material may be cloth. In other embodiments, the flexible material may be another type of relatively soft, flexible material such as fabric, a relatively soft, flexible polymer (e.g., silicone), or the like. When made from a fabric, the fibers of the fabric can be made of any of various biocompatible materials, such as polyethylene terephthalate (PET). The fabric can be a woven fabric, a non-woven fabric, or a pile fabric (e.g., velvet, velour, etc.) having tufts or loops of fibers extending from a woven base layer. Any of the various fabrics disclosed in U.S. Publication No. 2019/0192296, which is incorporated herein by reference, can be used to form the cushioning element 310 and other embodiments of cushioning elements disclosed herein.

In some embodiments, as shown in FIG. 7, the cushioning element 310 comprises a plurality of folds 312 arranged over and extending across a distal (e.g., distal-most) edge 314 of the apex 308 and forming a distal surface (or layer) 316 of the cushioning element 310. In this way, the plurality of folds 312 are formed over and across the tip of the apex 308. The plurality of folds 312 may extend between an inner layer 318 and an outer layer 320 of the cushioning element 310, where the inner layer 318 covers an inner surface of the corresponding apex 308 and the outer layer 320 covers an outer surface of the corresponding apex 308. The inner and outer layers may be relative to a central longitudinal axis of the valve 300 (not shown in FIG. 7) which extends through a center of the valve 300. In this way, the inner layer 318 is arranged closer to the central longitudinal axis than the outer layer 320. As shown in FIG. 7, the leaflets 304 are arranged on an inner surface of the frame 302 of the valve 300.

While the cushioning elements 310 are each shown with four folds 312, in alternate embodiments, each cushioning element 310 may include more or less than four folds (e.g., three, five, six, or the like).

In some embodiments, the inner layer 318 and the outer layer 320 may be secured (e.g., stitched) together, around both sides of the apex 308.

As shown in the embodiment of FIG. 7, while the inner layer 318 and the outer layer 320 may extend from the distal surface 316 to a base 322 of the apex 308, the plurality of folds 312 may not extend to the base 322. By covering at least the distal edge (e.g., tip) 314 of each apex 308, the cushioning elements 310 may reduce abrasion between the apices 308 and an inner surface of a sheath during delivery of the valve 300 to the target implantation site, thereby reducing degradation to the sheath and/or the valve.

It should be understood that references to the distal and proximal ends of the prosthetic valve refer to the positions of the ends of the valve during delivery. For example, in FIG. 7, an inflow end of the prosthetic valve 300 is referred to the distal end of the prosthetic valve because it is positioned distal to the outflow end during delivery. In other words, when the prosthetic valve 300 is mounted on the distal end portion of the delivery device (such as depicted in FIG. 4), the inflow end of the prosthetic valve is the distal-most end of the prosthetic valve and the outflow end of the prosthetic valve is the proximal-most end of the prosthetic valve. This arrangement is suitable for retrograde delivery of the prosthetic valve through the aorta to the native aortic valve. However, in other embodiments, the outflow end of the prosthetic valve can be the distal end of the prosthetic valve during delivery, depending on the particular delivery approach and the particular implantation location within the heart. For example, when delivering a prosthetic valve to the native mitral valve via a trans-septal delivery path, the outflow end of the prosthetic valve is the distal-most end of the prosthetic valve. Thus, the cushioning elements 310 (and all other embodiments of cushioning elements disclosed herein) can be mounted on the inflow end or the outflow end of the prosthetic valve, depending on the particular delivery approach and the particular implantation location within the heart for the procedure.

Further, in other embodiments, the cushioning elements 310 (and all other embodiments of cushioning elements disclosed herein) can be mounted on both the inflow end and the outflow end of the prosthetic valve. In still other embodiments, the cushioning elements 310 (and all other embodiments of cushioning elements disclosed herein) can be mounted only on the apices of the proximal end of the prosthetic valve. Thus, any disclosure in the present application that refers to the distal end of a prosthetic valve can be applied to the proximal end of the prosthetic valve.

In alternate embodiments, the plurality of folds of the cushioning elements may extend to the base of each apex, as shown by the embodiment presented in FIG. 8. Specifically, FIG. 8 shows a single apex 308 of the valve 300 covered by a cushioning element 330, according to a second embodiment. The cushioning element 330 comprises an inner layer 332 (similar to inner layer 318) covering an inner surface of the apex 308, an outer layer 334 (similar to outer layer 320) covering an outer surface of the apex 308, and a distal layer 336 defining a distal surface of the cushioning element and extending radially between the inner layer 332 and outer layer 334 and across the distal edge 314 (not visible in FIG. 8) of the apex 308. Each of the inner layer 332 and the outer layer 334 extend, in an axial direction relative to the central longitudinal axis of the valve 300, from the distal layer 336 to the base 322 of the apex 308.

The cushioning element 330 further includes a plurality of folds 338 arranged between the inner layer 332 and the outer layer 334. As shown in FIG. 8, each fold of the plurality of folds 338 extends from the distal layer 336 to the base 322 of the apex 308. In this way, an entirety of the apex 308 (not just the distal edge) is covered (e.g., encased) by the cushioning element 330.

In some embodiments, the plurality of folds 338 may be secured (e.g., stitched) to one another. In some embodiments, the plurality of folds 338 may be additionally or alternatively secured (e.g., stitched) to the inner layer 332 and the outer layer 334.

Figure 9:
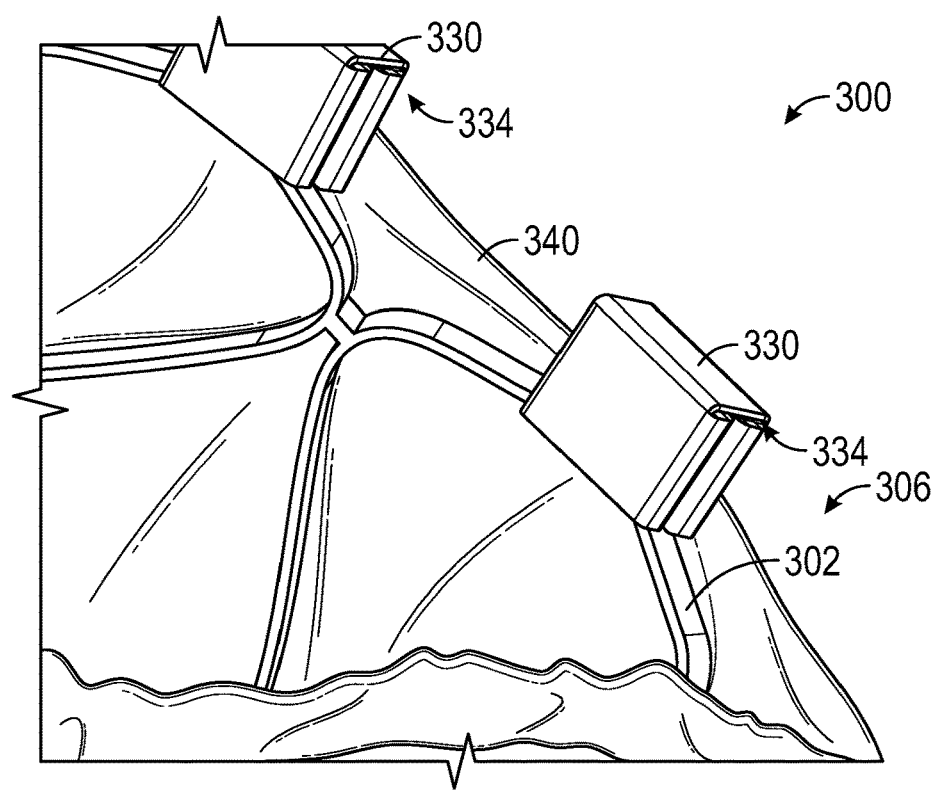
FIG. 9 shows the cushioning element of FIG. 8 secured to an outer skirt of the valve.

FIG. 9 shows the cushioning element 330 of FIG. 8 secured to an outer skirt 340 of the valve 300. As shown in FIG. 9, the outer skirt 340 may be arranged around an outside (e.g., outer surface) of the frame 302, at the distal end 306 of the valve 300. In some embodiments, the outer skirt 340 may be similar to the outer skirt 18 shown in FIG. 1.

Each cushioning element 330 is secured to the outer skirt 340. For example, as shown in FIG. 9, one or more surfaces of the cushioning element 330, such as the outer surface 334, may be sutured (e.g., stitched) to the outer skirt 340. In alternate embodiments, the cushioning element 330 may be secured to the outer skirt 340 via another means, such as an adhesive, staple, or other securing element.

Figure 10:
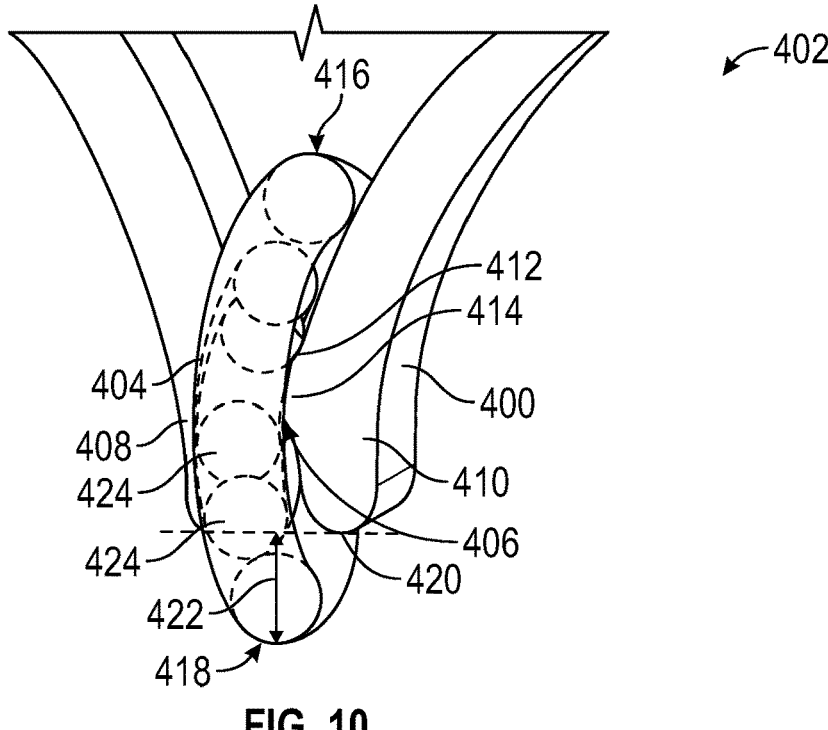
FIG. 10 is a partial view of a single apex of a prosthetic valve covered by a cushioning element, according to a third embodiment.

FIG. 10 shows another embodiment of a cushioning element covering an apex of a prosthetic valve. Specifically, FIG. 10 shows an apex 400 of a prosthetic heart valve (e.g., valve) 402 and a cushioning element 404 covering the apex 400 (only a portion of the valve and a single apex is shown in FIG. 10). The apex 400 comprises a notch 406 arranged between two distally extending arms, or struts, 408 and 410, of the frame that converge to form the apex 400. The notch 406 opens away from an end 412 of an open cell of the frame opposite the apex 400. A mid-portion 414 of the apex 400 is arranged between the cell end 412 and the notch 406.

The cushioning element 404 is looped around the mid-portion 414 of the apex 400, extending through the open cell and the notch 406. In some embodiments, the cushioning element 404 comprises a suture, yarn, string, rope, thread, or cable material repeatedly looped around the mid-portion 414 of the apex 400, thereby forming a soft, cushioning element 404 comprising multiple, overlapping loops 424 of material.

The cushioning element 404 has a proximal end 416 arranged at the proximal, cell end 412 of the apex 400 and a distal end 418 arranged at and overlaying and extending beyond a distal edge 420 of the apex 400 (the distal edge 420 formed at the distal edge of each of the distally extending arms 408, 410). A distance 422 designates the distance between the distal edge 420 of the apex 400 and the distal end 418 of the cushioning element 404. The material forming the cushioning element 404 may be repeatedly looped around the mid-portion 414 of the apex 400 until the distance 422 reaches a desired value (e.g., thickness value) that may be selected to adequately shield the apex 400 from contacting (e.g., having direct contact with) the inner wall of the delivery sheath during a valve delivery process, as explained above.

For example, instead of the apex 400 having direct contact with the inner wall of the sheath, during the valve delivery process, the distal end 418 of the cushioning element 404 may contact the inner wall of the sheath. However, since the cushioning element 404 comprises a relatively soft, flexible material (e.g., instead of a relatively hard, metal material), contact between the cushioning element 404 and sheath may not cause degradation to either the sheath or the valve.

In alternate embodiments, the cushioning element 404 may comprise only a single loop 424 of a relatively thicker suture, yarn string, rope, thread, or cable material.

Figures 11, 12, 13:
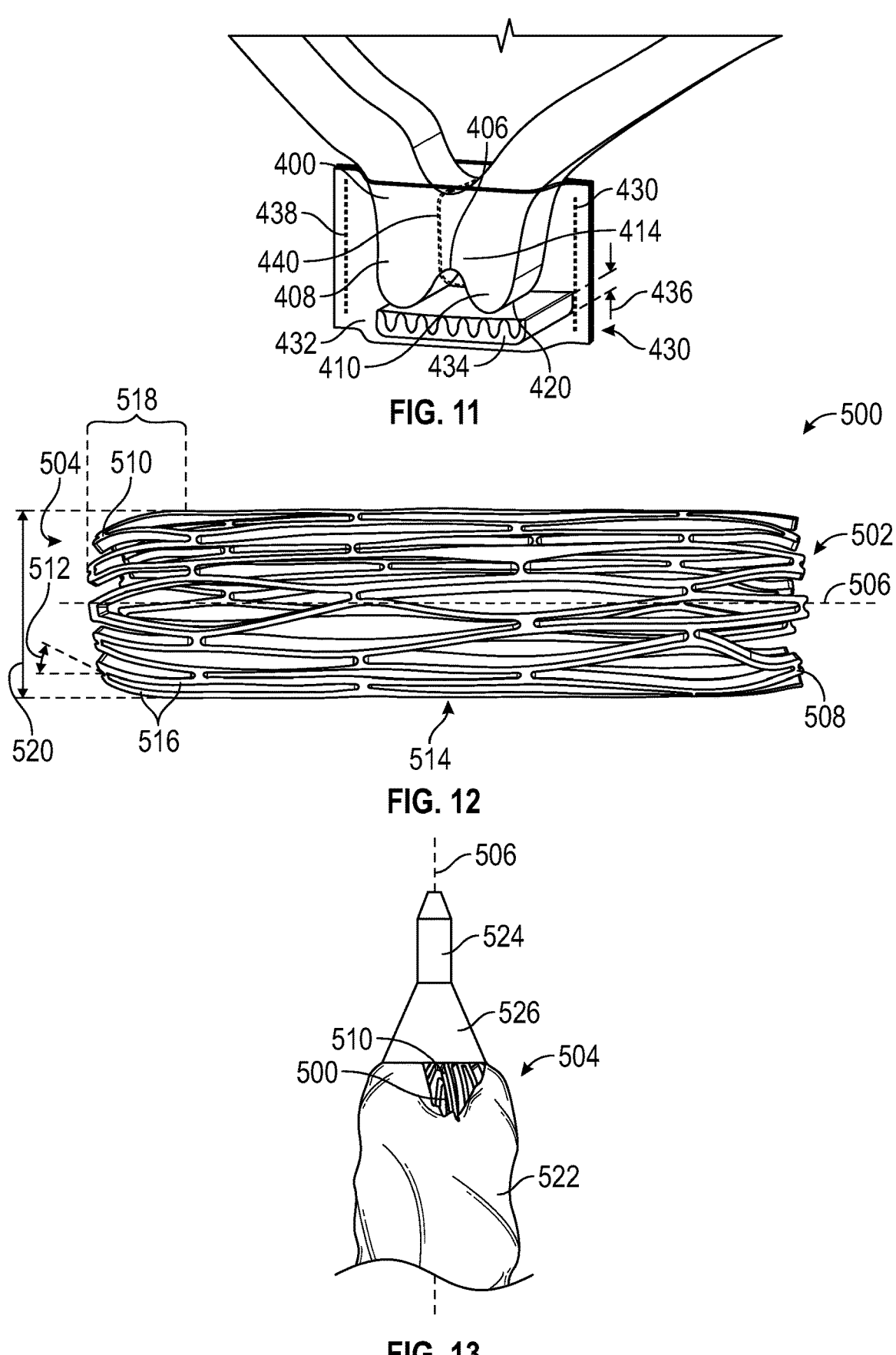
FIG. 11 is a partial view of a single apex of a prosthetic valve covered by a cushioning element, according to a fourth embodiment.
FIG. 12 is a side view of a valve frame, which may be included in a prosthetic heart valve, having inwardly curved apices arranged at a distal end of the valve frame, according to an embodiment.
FIG. 13 is side view of a distal portion of the valve frame of FIG. 12 with an outer skirt arranged around an outer surface of the valve frame and a nosecone extending distally from a distal end of the valve frame.

FIG. 11 shows yet another embodiment of a cushioning element covering an apex of a prosthetic valve, which may be the same as or similar to the valve 402 shown in FIG. 10. Specifically, FIG. 11 shows a single apex 400 of the valve 402 and a cushioning element 430 covering the apex 400.

The cushioning element 430 includes a pocket 432 surrounding the apex 400 and a padding element 434 arranged within an interior of the pocket 432. Specifically, as shown in FIG. 11, the padding element 434 is arranged within a bottom portion of the pocket 432, distal to the distal edge 420 of the apex 400. For example, the padding element 434 is arranged within the pocket 432, between the distal edge 420 of the apex 400 and an internal, distal edge of the pocket 432. The padding element 434 is further retained within the interior of the pocket 432 via sidewalls of the pocket 432, with the sidewalls being folded around the apex 400.

In some embodiments, the padding element 434 may cover an entirety of the distal edge 420 of the apex 400 (e.g., extending across the distal ends of each of the two distally extending arms, 408 and 410, and from an inner surface to an outer surface of the apex 400). In alternate embodiments, the padding element 434 may cover a portion of the entirety of the distal edge 420.

The padding element 434 may have a thickness 436 selected to reduce abrasion between the apex 400 and the internal wall of the sheath. In some embodiments, the padding element 434 may comprise a relatively soft and flexible material, such as sutures, yarns, cables, fabric (any type of fabric disclosed herein), sponge, or the like.

In some embodiments, the pocket 432 may comprise a relatively soft, flexible material (e.g., fabric, flexible polymer, or the like) folded over and around the apex 400. For example, as shown in FIG. 11, the pocket 432 may extend around the apex 400, from an inner surface to an outer surface of the apex 400 and, in an axial direction, from at least a portion of the mid-portion 414 of the apex 400 to a distance past the distal edge 420.

Overlapping folds of the pocket 432, at ends of the pocket 432, may be secured to one another via a fastening element 438. As shown in FIG. 11, the fastening element 438 is a line of stiches along a periphery of the pocket 432. However, in alternate embodiments, the fastening element 438 may be another type of fastening element such as staples, adhesive, or the like.

In some embodiments, the pocket 432 can be further fastened (e.g., stitched) directly to the apex 400, for example along a central stitch line 440. For example, as shown in FIG. 11, the pocket 432 is fastened around the mid-portion 414 of the apex 400 via the central stitch line 440.

In some embodiments, the padding element 434 may be fixed to the pocket 432, for example, via stitching or other fastening means (e.g., adhesive, staples, or the like).

In some embodiments the padding element 434 may be directly attached to the distal edge 420 of the apex 400, without the pocket 432 (e.g., there may be no pocket around the apex 400). Attachment of the padding element 434 to the distal edge 420 can be accomplished by various fastening means, such as stitching, gluing, and the like.

In this way, a cushioning element covering a plurality of apices arranged at a distal end of a frame of a prosthetic heart valve may be adapted to shield the apices from direct contact with inner walls of a delivery sheath of a delivery system, during a valve delivery process, thereby reducing abrasion to and degradation of the sheath and/or valve.

In another embodiment, apices arranged at a distal end of a frame of a prosthetic valve may be inwardly curved, relative to a central longitudinal axis of the valve, at least when the valve is in a radially compressed state (e.g., crimped state around a delivery device), in order to mitigate a likelihood of abrasion of inner walls of the delivery sheath with apices of the prosthetic valve. FIGS. 12-13 show embodiments of a frame, which may be used as the frame of a prosthetic heart valve, having inwardly bent apices at a distal end of the frame, the distal end adapted to be positioned adjacent to a nosecone and/or distal shoulder of a delivery device when the valve is crimped to a valve retaining portion of the delivery device. In some embodiments, the frame depicted in FIGS. 12-13 may be used as the frame of a prosthetic heart valve, such as the prosthetic heart valve 10 shown in FIG. 1 and/or prosthetic heart valve 50 shown in FIGS. 2A-2B.

Turning first to FIG. 12, a frame 500, which may be included in a prosthetic heart valve, having inwardly curved apices arranged at a distal end is shown. The frame 500 shown in FIG. 12 is in a compressed (e.g., non-expanded) state (e.g., configuration) which may occur after crimping the prosthetic heart valve to a portion of a delivery device (e.g., around a balloon). As shown in FIG. 12, the frame 500 has a proximal end 502 and a distal end 504. The frame 500 also has a central longitudinal axis 506, which may also be a central longitudinal axis of the prosthetic heart valve in which it is included. The proximal end 502 includes a plurality of proximal apices 508 and the distal end 504 includes a plurality of distal apices 510. The plurality of proximal apices 508 are spaced apart from one another around a circumference of the proximal end 502 and the plurality of distal apices 510 are spaced apart from one another around a circumference of the distal end 504.

Each distal apex 510 is curved (e.g., bent) radially inward, toward the central longitudinal axis 506. For example, as shown in FIG. 12, each distal apex 510 is curved inward at an angle 512, relative to a line parallel with the central longitudinal axis 506. As a result, the distal end 504 of the frame 500 may curve inward relative to at least a central portion 514 of the frame 500 which may be arranged approximately parallel with the central longitudinal axis 506. As shown in FIG. 12, the central portion 514 is arranged between the proximal end 502 and the distal end 504.

In some embodiments, as shown in FIG. 12, the plurality of proximal apices 508 are also curved inward, toward the central longitudinal axis 506. However, in some embodiments, the angle of inward curvature of the proximal apices 508 may be less than that of the angle 512 of the distal apices 510.

In some embodiments, the angle 512 is less than 45 degrees. In other embodiments, the angle 512 is in a range of 15 to 40 degrees.

In other embodiments, the plurality of proximal apices 508 may not be inwardly curved, and instead, each proximal apex 510 may be oriented in a direction parallel to the central longitudinal axis 506.

The angling or curving inward of the distal apices 510 may create a radius (e.g., a varying radius on an outer diameter of the frame of the valve). This radius may be arranged tangential to the sheath.

The frame 500 further includes a plurality of struts 516. Each distal apex 510 may be formed by meeting ends of adjacent struts 516. In some embodiments, as shown in FIG. 12, at least a portion of the adjacent struts 516 forming the distal apices 510 are curved inward toward the central longitudinal axis 506. As such, a distal portion 518 of the frame 500, arranged at the distal end 504, may be curved inward toward the central longitudinal axis 506 from the central portion 514 of the frame 500. As a result, a diameter 520 of the frame 500 at the distal end 504 is smaller than a diameter of the central portion 514 of the frame 500. In some embodiments, the diameter 520 may also be smaller than a dimeter of the frame 500 at the proximal end 502.

Additionally, as seen in FIG. 12, the central portion 514 of the frame 500, arranged between the distal portion 518 and a proximal portion at the proximal end 502, which is arranged parallel with the central longitudinal axis 506, may be a longest (in a direction of the central longitudinal axis 506) portion of the frame 500. Said another way, a majority of the frame 500, including the central portion 514, may not be curved inward toward the central longitudinal axis 506.

FIG. 13 shows a distal portion of the frame 500 with an outer (e.g., external) skirt 522 arranged around an outer surface of the frame 500 and extending in a proximal direction from the distal end 504 of the frame 500. In FIG. 13, a portion of the outer skirt 522 is removed, for illustration purposes, to expose the inwardly curved (in the radial direction relative to the central longitudinal axis 506) distal apices 510.

FIG. 13 also depicts a nosecone 524 of a delivery device (to which the frame 500 may be crimped) arranged distally to the distal end 504 of the frame 500. In some embodiments, as shown in FIG. 13, the nosecone 524 may include or be coupled to a distal shoulder 526 of the delivery device.

As shown in FIG. 13, bending the distal apices 510 inward, toward the central longitudinal axis 506, closes a circumferential gap between adjacent distal apices 510 and narrows the diameter of the frame 500 at the distal end 504. As a result, contact between the distal apices 510 and inner walls of a delivery sheath, during a valve delivery process, may be reduced, thereby reducing degradation of the sheath and/or valve. In this way, the distal apices 510 are spaced away from walls of the delivery sheath without enlarging an outer diameter of the prosthetic valve.

In yet another embodiment, a nosecone of a delivery device may be configured with a jacket adapted to cover apices arranged at a distal end of a frame of a prosthetic valve during a delivery process of the valve to a target implantation site via the delivery device, in order to mitigate a likelihood of abrasion of inner walls of a delivery sheath with the prosthetic valve. FIGS. 14-18 show embodiments of such a jacket for a nosecone of a delivery device.

Turning first to FIGS. 14-16, a delivery device, including a nosecone with an attached nosecone jacket, for delivering a prosthetic valve crimped thereon to a target implantation site is shown. Specifically, FIGS. 14-16 show a portion of a delivery device 600 with a central longitudinal axis 618. The delivery device may be similar to the delivery device 100 shown in FIGS. 3-5 and/or delivery device 204 shown in FIG. 6.

As shown in FIGS. 14-16, the delivery device 600 includes an inflatable balloon 602 and a nosecone 604. The balloon shoulders (e.g., proximal shoulder and distal shoulder) and shafts of the delivery device 600 are omitted for simplicity of illustration in FIGS. 14-16, but may be included within the balloon, as shown in FIGS. 3 and 4, for example. A prosthetic valve 606 having a frame 608 is shown mounted on the balloon 602, on a valve retaining portion 610 of the balloon 602. The frame 608 may be crimped onto the valve retaining portion 610 of the balloon 602.

The frame 608 includes a proximal end 612 and a distal end 614, the distal end 614 arranged opposite the proximal end 612. The distal end 614 is arranged adjacent to the (distal) end of the balloon 602 connected to the nosecone 604. The distal end 614 is arranged closer to a proximal end of the nosecone 604 than the proximal end 612 of the frame 608. As explained above, the distal end 614 of the frame 608 includes a plurality of apices arranged around a circumference of the distal end 614 (not shown in FIGS. 14-16).

As shown in FIGS. 14-16, a nosecone jacket 616 is attached to the nosecone 604 (e.g., attached to a body of the nosecone). Specifically, the nosecone jacket 616 includes a first end 620 (e.g., edge) attached to the nosecone 604 and a free, second end (e.g., edge) 622 that is unattached to the nosecone 604 and any other component of the delivery device 600. For example, the first end 620 may be directly coupled (e.g., fixed) to the body of the nosecone 604 while the second end 622 is free to translate between positions that are proximal and distal to the first end, relative to the central longitudinal axis 618 of the delivery device. For example, in some embodiments, the second end 622 is unattached to the nosecone 604 along an entire edge of the second end 622.

In some embodiments, the first end 620 is directly coupled to a proximal end of the nosecone (e.g., nosecone body) 604. In some embodiments, the proximal end of the nosecone 604 may be coupled to a distal shoulder of the delivery device 600, the distal shoulder supporting a distal portion of the balloon 602.

The nosecone jacket 616 may comprise a flexible material. For example, in some embodiments, the nosecone jacket 616 may comprise a flexible material such as fabric (any type of fabric disclosed herein), tissue, a polymeric sheet, and/or the like. In this way, the free, second end 622 of the nosecone jacket 616 may be adapted to translate axially, along the central longitudinal axis 618, between positions that are distal to the first end 620 (e.g., downstream of the first end) and proximal to the first end 620 (e.g., upstream of the first end). Examples of different positions of the second end 622 of the nosecone jacket 616, during various points in a valve delivery process, are shown in FIGS. 14-16, as described further below.

A valve delivery process may include crimping (e.g., radially compressing) the prosthetic valve 606 (e.g., the frame 608 of the prosthetic valve) around the balloon 602 of the delivery device 600. The valve 606 may be retained, in its crimped (e.g., radially compressed) state, on the valve retaining portion 610 of the balloon 602, with the distal end 614 of the frame 608 arranged proximate to (e.g., adjacent to) the nosecone 604 (e.g., the distal end 614 is arranged closer to the nosecone 604 than the proximal end 612 of the frame 608). In this way, the apices arranged at the distal end 614 of the frame 608 may be facing the distal portion of the balloon 602 and the nosecone 604. The delivery device 600, including the crimped prosthetic valve 606, may be advanced through a delivery sheath inserted into a lumen (e.g., blood vessel) of a patient and to a target implantation site (e.g., target site for deploying and implanting the valve 606). Deploying the valve 606, once the target implantation site is reached, may include inflating the balloon 602 to expand the valve 606 from its crimped state. In some embodiments, the sheath and the delivery device 600 may be included in a transcatheter delivery system.

FIG. 14 shows the prosthetic valve 606 in a crimped (e.g., radially compressed) state on the delivery device 600, prior to insertion of the delivery device 600 into a delivery sheath of the delivery system. In this state, the second end 622 of the nosecone jacket 616 may be oriented in any direction. In some embodiments, as shown in FIG. 14, the second end 622 may be oriented distally away from, relative to the central longitudinal axis 618, the first end 620 of the nosecone jacket 616 and the frame 608.

According to some embodiments, the nosecone jacket 616 can be oriented distally away from the frame 608 prior to crimping the valve 606 onto the balloon 602, in order to prevent the nosecone jacket 616 from being crimped over the frame 608. According to other embodiments, the nosecone jacket 616 can be oriented in a proximal direction (as shown in FIG. 15, as described further below) prior to crimping, thereby assuming such an orientation in a crimped state of the valve 606.

FIG. 15 shows the prosthetic valve 606 in a crimped state on the delivery device 600, during valve delivery through an introducer (e.g., delivery) sheath of the delivery system. Due to the advancement of the delivery device 600 and valve 606 in a distal direction 624, the nosecone jacket 616 is inverted such that the second end 622 extends proximally to (and away from) the first end 620, towards the frame 608 of the valve 606. In this state, during valve delivery and advancement of the delivery device 600 through the sheath, the second end 622 is oriented such that the jacket 616 at least partially covers the distal end 614 of the frame 608, as shown in FIG. 15. In other embodiments, the jacket 616 can be inverted by the user to cover the distal end 614 of the frame prior to inserting the delivery device and the prosthetic valve into the introducer sheath.

For example, a length of the nosecone jacket 616, the length arranged between the first end 620 and the second end 622, may be selected such that in the state shown in FIG. 15, its second end 622 is positioned proximal to the distal end 614 of the frame 608, thereby covering the distal end 614 and its distal apices during valve delivery through the delivery sheath.

As a result, the nosecone jacket 616 provides an atraumatic cover to the distal end 614 of the valve 616, thereby preventing the distal apices from directly contacting the inner walls of the delivery sheath. For example, during advancing the distal end of the delivery device 600 to a target implantation site for the prosthetic valve, the nosecone jacket 616 can cover the distal end 614 of the frame 608, thereby providing a protective barrier between the plurality of apices of the distal end 614 of the frame 608 and the sheath and/or the patient's vasculature.

FIG. 16 shows the prosthetic valve 606 in an expanded state after inflation of the balloon 602, after reaching the target implantation site. During inflation of the balloon 602, the frame 608 expands (in a radial direction relative to the central longitudinal axis 618) and the nosecone jacket 616 slides over the distal portion 626 of the balloon 602 and distally away from the distal end 614 of the frame 608.

In some embodiments, the length of the nosecone jacket 616 may be further selected such that in the state shown in FIG. 16, the second end 622 will slide away, distal to the frame 608, and it will no longer cover the distal end 614 of the frame 608.

In some embodiments, when the balloon 602 is deflated (after inflation), the nosecone 604 can be retracted while the nosecone jacket 616 can assume a distal orientation (similar to its orientation sown in FIG. 14), thereby enabling the nosecone 604 to be pulled out, through the inner lumen of the now expanded valve 606.

In this way, the nosecone jacket 616 is translatable between a proximal, first position where the second end 622 is arranged over a distal end 614 of the frame 608 of the prosthetic valve 606 crimped onto the balloon 602 of the delivery device 600 (as shown in FIG. 15) and a distal, second position where the second end 622 is arranged distally away from the distal end 614 of the frame 608 (as shown in FIG. 16 and also FIG. 14).

Figure 17:
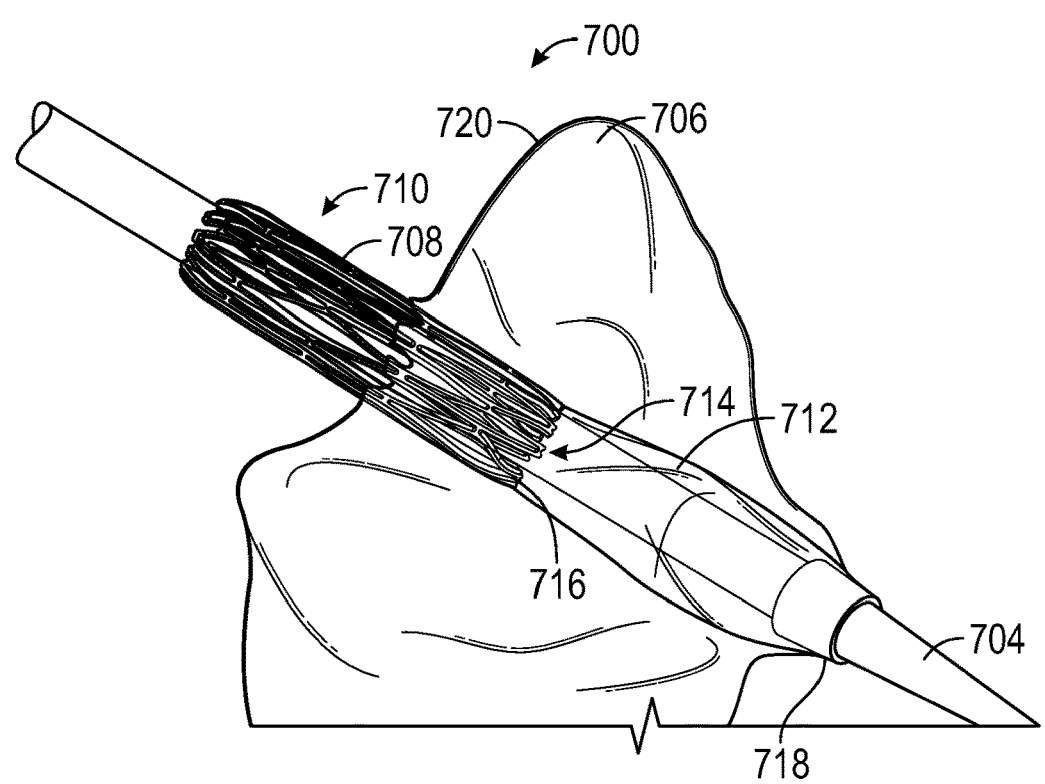
FIG. 17 shows a first perspective view of a delivery device including a nosecone with a nosecone jacket, according to an embodiment.
Figure 18:
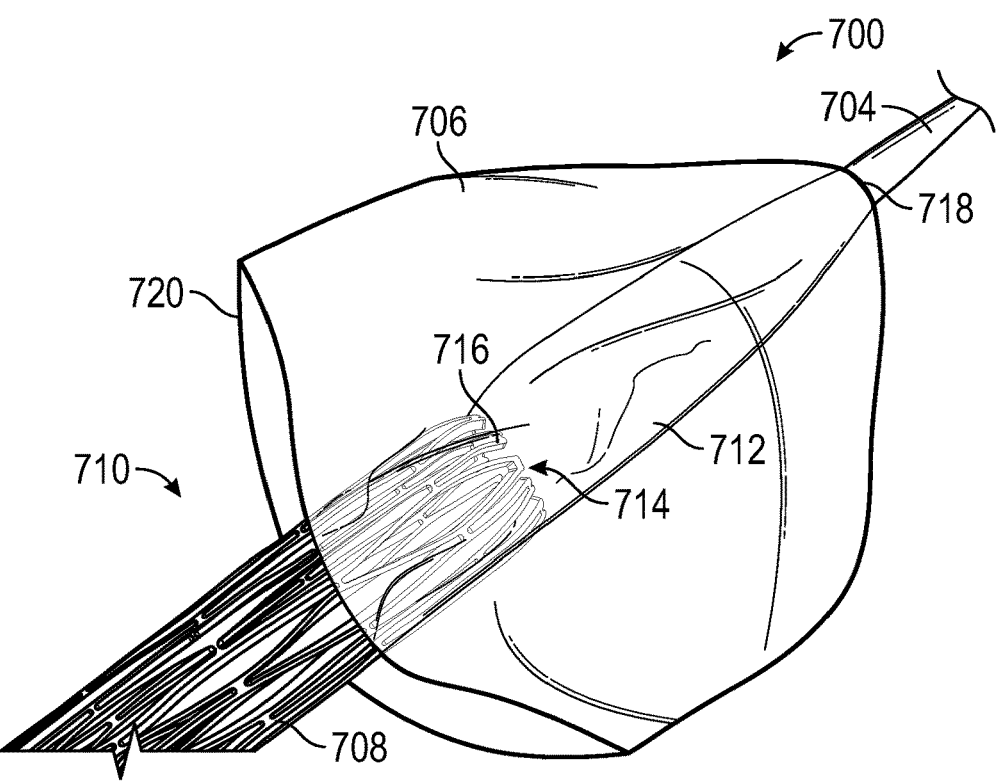
FIG. 18 shows a second perspective view of the delivery device of FIG. 17.

FIGS. 17 and 18 show perspective views of a delivery device 700 including a nosecone 704 with a nosecone jacket 706, according to an embodiment. As shown in FIGS. 17 and 18, a frame 708 of a prosthetic valve 710 is crimped around a balloon 712 of the delivery device 700. A distal end 714 of the frame 708 includes a plurality of distal apices 716 arranged around a circumference of the frame 708. The distal end 714 is arranged proximate to the nosecone 704.

The nosecone jacket 706 shown in FIGS. 17 and 18 may be similar to and function similarly to the nosecone jacket 616 shown in FIGS. 14-16, as described above. For example, the nosecone jacket 706 shown in FIGS. 17 and 18 may be in the state shown in FIG. 15, which may occur during valve delivery when the delivery device 700 is being advanced through a delivery sheath of the delivery system, toward a target implantation site for the valve 710.

As shown in FIGS. 17 and 18, the nosecone jacket 706 includes a fixed end 718 coupled to a proximal end of the nosecone 704 and a free end 720 that is not coupled to the nosecone 704 or any other component of the delivery device 700. In this way, the free end 720 is free to move back and forth across a length of the delivery device and relative to the fixed end 718. As shown in FIGS. 17 and 18, the free end 720 is arranged in a proximal position where the free end 720 surrounds and covers (e.g., overlays) the distal end 714 of the frame 708. In this way, the nosecone jacket 706 covers and shields the distal apices 716 from the surrounding environment (external to the nosecone jacket 706), including an inner wall of the delivery sheath. As a result, degradation of the delivery sheath and/or the prosthetic valve due to direct contact between the distal end of the valve and the inner wall of the sheath may be reduced.

In other embodiments, a nosecone jacket coupled to the nosecone and covering the distal apices of the prosthetic valve during delivery of the prosthetic valve to the target implantation site may comprise an elastic material, such as rubber in one example, and may have a geometry that fits or conforms to the distal end of the valve, when the prosthetic valve is in a crimped state. Since the nosecone jacket comprises an elastic material, that is adapted to stretch for example, the nosecone jacket can allow the prosthetic valve to expand into its expanded state, at the implantation site, without needing to be removed from the prosthetic valve. The nosecone jacket can be releasable from the nosecone after deployment of the prosthetic valve, such as by removing or cutting sutures that connect the nosecone jacket to the nosecone. Moreover, the nosecone jacket may also comprise a biocompatible and/or biodegradable material that remains attached to the implanted valve, for at least a period of time. In alternate embodiments, this type of nosecone jacket may be removable from the prosthetic valve after implantation via the delivery device or an additional component.

Figure 19:
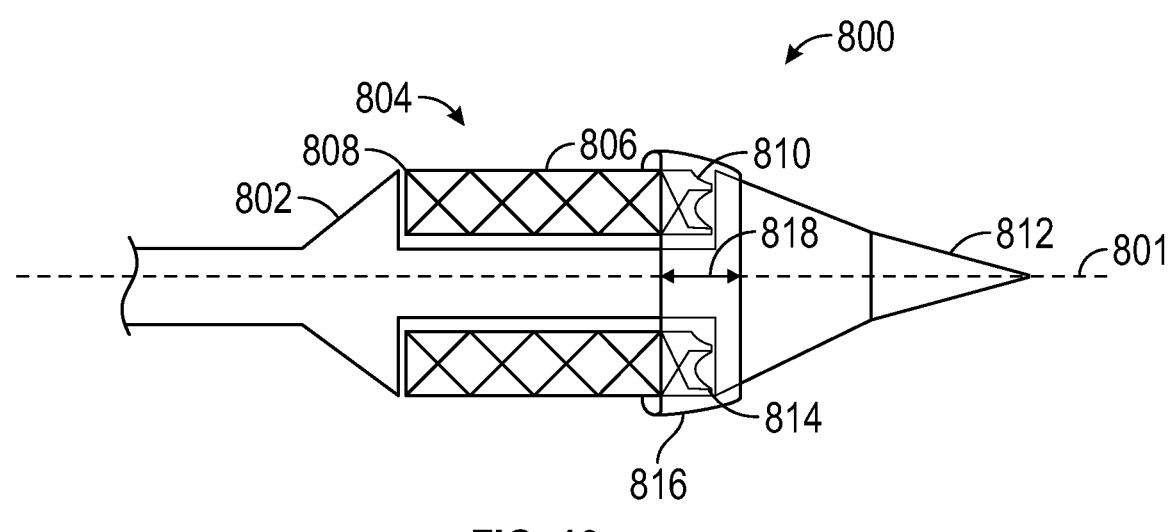
FIG. 19 is a schematic showing a bio-resorbable cover for apices arranged at a distal end of a frame of a prosthetic valve, according to an embodiment.

In another embodiment, a bio-resorbable element may be adapted to cover apices arranged at a distal end of a frame of a prosthetic valve, in order to mitigate a likelihood of abrasion of inner walls of the delivery sheath with the prosthetic valve. FIG. 19 shows an embodiment of a bio-resorbable cover for apices arranged at the distal end of the frame of the prosthetic valve.

Specifically, FIG. 19 shows a portion of a delivery device 800 with a central longitudinal axis 801. The delivery device may be similar to the delivery device 100 shown in FIGS. 3-5 and/or delivery device 204 shown in FIG. 6. The delivery device 800 includes an inflatable balloon 802 and a nosecone 812. The balloon shoulders (e.g., proximal shoulder and distal shoulder) and shafts of the delivery device 800 are omitted for simplicity of illustration in FIG. 19, but may be included within the balloon, as shown in FIGS. 3 and 4, for example. A prosthetic valve 804 having a frame 806 is crimped onto and around a valve retaining portion of the balloon 802. In some embodiments, the prosthetic valve 804 may be similar to one of the other prosthetic valves described herein, with reference to the figures (e.g., as shown in FIGS. 1-2B).

The frame 806 includes a proximal end 808 and a distal end 810, the distal end 810 arranged opposite the proximal end 808. The distal end 810 is arranged adjacent to the (distal) end of the balloon 802 connected to the nosecone 812. The distal end 810 is arranged closer to a proximal end of the nosecone 812 than the proximal end 808 of the frame 806. As explained above and shown schematically in FIG. 19, the distal end 810 of the frame 806 includes a plurality of apices 814 arranged around a circumference of the distal end 810.

As shown in FIG. 19, a bio-resorbable element (e.g., cover) 816 is arranged around the distal end 810 to cover the distal apices 814. In some embodiments, as shown in FIG. 19, the bio-resorbable element 816 may be a single element or cover that is wrapped around an entire circumference of the distal end 810 of the frame and covers each and every distal apex 814. In other embodiments, the bio-resorbable element may two or more elements, each covering at least one distal apex 814.

In some embodiments, the bio-resorbable element 816 may be an element that is wrapped, as a single layer, around the circumference of the distal end 810. In other embodiments, the bio-resorbable element 816 may be an element that is wrapped in multiple layers around the circumference of the distal end 810.

A thickness of the bio-resorbable element 816, in a radial direction relative to the central longitudinal axis 801, may be selected based on a desired material of the bio-resorbable element, desired number of wraps or layers, and/or a desired resorption rate (as explained further below).

A width 818 of the bio-resorbable element 816 may be selected based on a size and/or length of the distal apices 814 so that the bio-resorbable element 816 fully covers the distal apices 814 or at least covers a distal edge of the distal apices 814. As shown in FIG. 19, the width 818 of the bio-resorbable element 816 extends from a location proximal to (e.g., upstream of) a base of the distal apices 814 to a location distal to (e.g., downstream of) distal ends of the distal apices 814. In some embodiments, as shown in FIG. 19, the bio-resorbable element 816 may extend distally past the distal apices an onto a distal portion of the balloon 802.

The bio-resorbable element 816 may comprise a dissolving biofilm, a bio-resorbable polymer, or the like. Some non-limiting examples of possible bio-resorbable polymers include polylactide (PLA), poly-L-lactide (PLLA), polyglycolide (PGA), poly-e-Caprolactone (PCL), trimethylene carbonate (TMC), poly-DL-lactide (PDLLA), poly-b-hydroxybutyrate (PBA), poly-p-dioxanone (PDO), poly-b-hydroxypropionate (PHPA), and poly-b-malic acid (PMLA).

The bio-resorbable element 816 may only be necessary for covering and shielding the distal apices 814 from directly contacting an inner wall of a delivery sheath during a valve delivery process and is no longer needed once the valve 804 reaches and is positioned at the target implantation site. Thus, the bio-resorbable element 816 is adapted to degrade (e.g., dissolve or resorb) in a pre-determined time frame that is based on a time to advance the prosthetic valve 804, crimped on the delivery device 800, through a sheath to the desired implantation site in a patient. The resorption rate of the bio-resorbable element 816 may be controlled by a variety of selectable parameters, such as the polymer material of the bio-resorbable element, additives to the base material of the bio-resorbable element, processing techniques, and the like. In some embodiments, the material of the bio-resorbable element 816, including any additives or specific processing techniques, may be selected to achieve a desired resorption rate. The desired resorption rate may be selected so that the bio-resorbable element 816 maintains its material integrity (to cover the distal apices) long enough to cover the distal apices 814 during delivery of the valve 804 to the target implantation site, and degrade prior to (e.g., in a desired time frame from) an end of the implantation procedure.

In alternative embodiments, the bio-resorbable element 816 can be configured to tear or break upon inflation of the balloon 802 to permit radial expansion of the prosthetic valve at the desired implantation site and then degrade inside the body at some time after deployment of the prosthetic valve. In some embodiments, the bio-resorbable element 816 can be formed with a score line or weakened portion (e.g., a thinner section formed along the length of the element 816) that facilitates tearing of the element 816 upon inflation of the balloon.

In this way, a bio-resorbable element or cover adapted to cover distal apices of a frame of a prosthetic valve may provide an atraumatic cover to the distal end of the valve, thereby preventing the distal apices from directly contacting the inner walls of the delivery sheath. The bio-resorbable element may be further adapted to dissolve or degrade just prior to or after valve implantation, once it is no longer needed during the valve delivery process.

Figure 20:
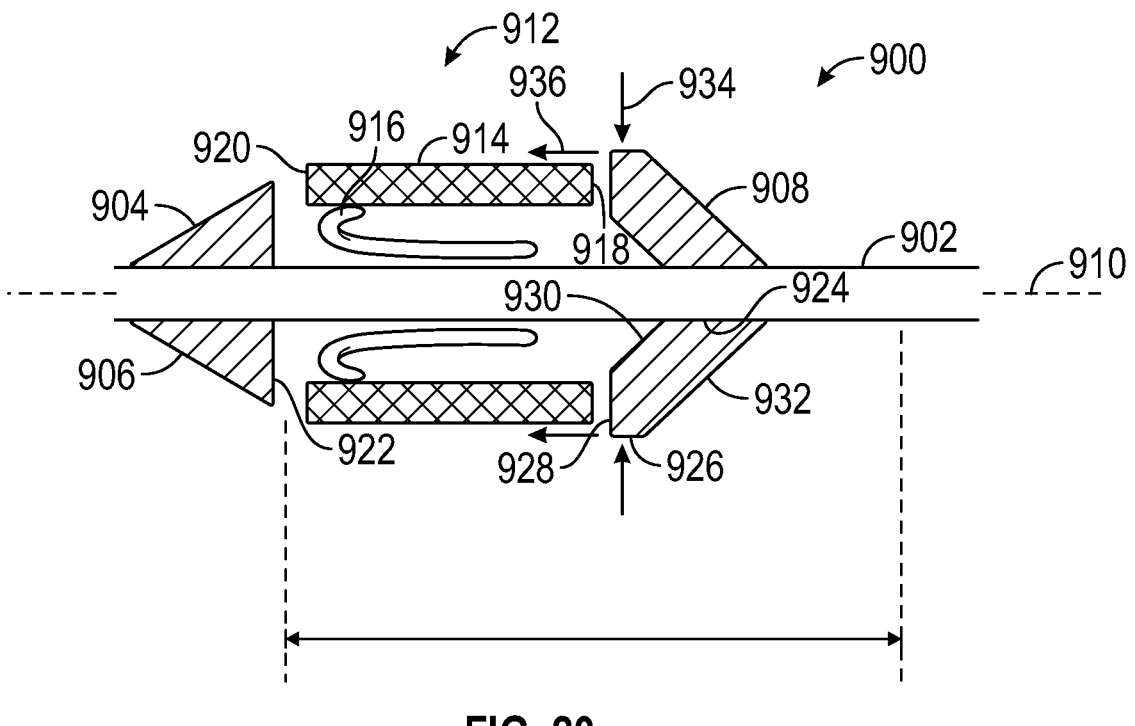
FIG. 20 is a schematic showing a first cross-sectional view of a delivery device for a transcatheter delivery system and forces imparted on a prosthetic valve arranged on a balloon of the delivery device by an adjustable, proximal shoulder during a valve crimping process, according to an embodiment.
Figure 21:
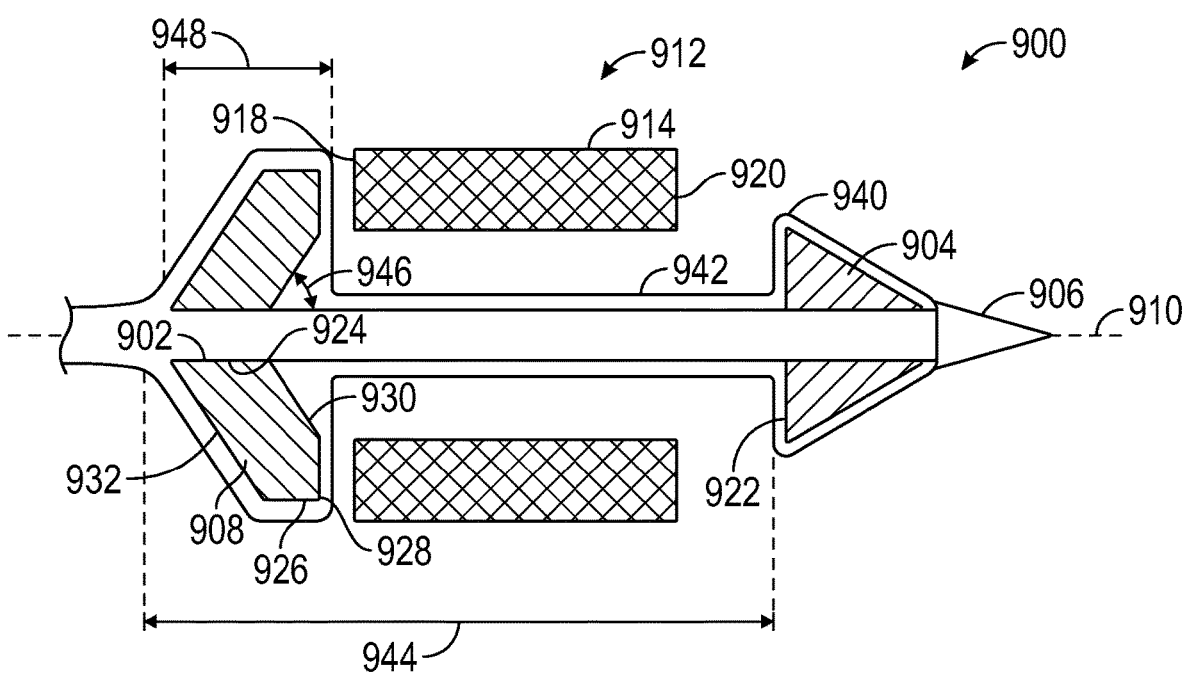
FIG. 21 is a schematic showing a second cross-sectional view of the delivery device of FIG. 20, in a partially crimped configuration.
Figure 22:
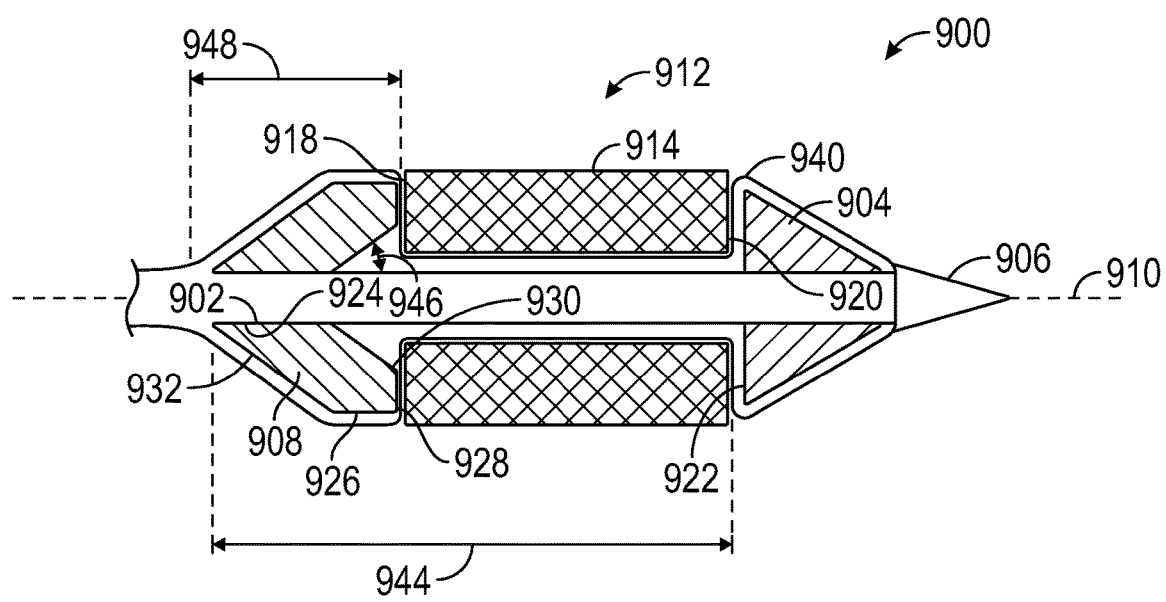
FIG. 22 is a schematic showing the second cross-sectional view of the delivery device of FIG. 20, in a fully crimped configuration.

In yet another embodiment, a delivery device adapted to deliver a prosthetic valve crimped thereon to a target implantation site, through an introducer sheath, may include a balloon shoulder assembly including an adjustable, proximal shoulder adapted to push the prosthetic valve in a distal direction, toward a distal shoulder (which may include or be coupled to a nosecone) of the balloon shoulder assembly, during crimping of the prosthetic valve onto a balloon, between the proximal and distal shoulders. As a result, an amount of space, in an axial direction, between the crimped valve and the distal shoulder and/or nosecone may be reduced, thereby reducing a likelihood of gap formation between the frame of the valve and the nosecone during valve delivery to the target implantation site via the delivery device. Thus, degradation to the delivery sheath and/or valve due to contact between the valve and sheath during valve delivery may be reduced. FIGS. 20-22 show an embodiment of a delivery device including an adjustable proximal shoulder adapted to reduce a spacing between a crimped valve and distal shoulder/nosecone of the balloon shoulder assembly.

Turning first to FIG. 20, a first cross-sectional view of a delivery device for a transcatheter delivery system, showing forces imparted on a prosthetic valve arranged on a balloon of the delivery device by an adjustable, proximal shoulder during a valve crimping process is shown. Specifically, FIG. 20 shows a portion of a delivery device 900 which may be part of a transcatheter delivery system including an introducer sheath (e.g., sheath 150 in FIG. 5) through which the delivery device 900 is advanced during a valve delivery process. The delivery device 900 includes a shaft (e.g., valve shaft) 902, a distal shoulder 904 mounted to a distal end of the shaft 902, and an adjustable, proximal shoulder 908 spaced apart from the distal shoulder 904, along a central longitudinal axis 910 of the delivery device 900.

In some embodiments, as shown in FIG. 20, a distal end of the distal shoulder 904 forms a nosecone 906. In other embodiments, as shown in FIGS. 21 and 22, the nosecone 906 may be arranged at and/or coupled to a distal end of the distal shoulder 904. In some embodiments, the distal shoulder 904 and the proximal shoulder 908 are annular parts that extend around an entire circumference of the shaft 902.

The delivery device 900 may include an inflatable balloon (not shown in FIG. 20, but shown in FIGS. 21 and 22, as described further below) arranged around a portion of the shaft 902, the distal shoulder 904, and the proximal shoulder 908.

A prosthetic valve (e.g., prosthetic heart valve) 912 is arranged around a portion of the shaft 902, between the distal shoulder 904 and the proximal shoulder 908. The valve 912 includes a frame 914 and leaflets 916. In some embodiments, the valve 912 may be similar to one of the prosthetic heart valves shown in FIGS. 1-2B, as described above. The frame 914 includes a proximal end 918 arranged adjacent to the proximal shoulder 908 and a distal end 920 arranged adjacent to the distal shoulder 904 and nosecone 906. The distal end 920 includes a plurality of distal apices arranged around a circumference of the distal end 920. A proximal edge 922 of the distal shoulder 904 (and/or nosecone 906) faces and is parallel to the proximal end 920 of the frame 914.

The proximal shoulder 908 is adjustable during crimping to minimize any gaps between the prosthetic valve and the proximal and distal shoulders. For example, the proximal shoulder 908 is flexibly attached at a proximal edge 924 along a portion of the shaft 902. As used herein, "flexibly attached" may refer to the ability of a remainder of the proximal shoulder to pivot (e.g., hinge or flex) relative to the proximal edge 924. For example, the flexible attachment of the proximal edge 924 to and around the shaft 902 may allow the proximal edge 924 to serve as a hinge about which a remainder of a body of the proximal shoulder 908 may pivot around, as described further below.

As shown in FIG. 20, the proximal edge 924 is a circumferential edge (e.g., arranged and extending around an entire circumference of the proximal shoulder 908) arranged parallel to an outer surface of the shaft 902.

The proximal shoulder 908 further includes an outer edge (also referred to herein as an outer surface) 926 arranged parallel with the central longitudinal axis 910. For example, the outer edge 926 is a circumferential edge arranged concentric with and parallel to an outer surface of the shaft 902. Additionally, the proximal shoulder 908 includes a distal edge 928 arranged perpendicular to the central longitudinal axis 910. For example, the distal edge 928 is a circumferential edge arranged perpendicular to the outer surface of the shaft 902.

The proximal shoulder 908 further includes an inner, inclined edge 930 arranged between the proximal edge 924 and the distal edge 928 that is angled relative to the central longitudinal axis 910. Additionally, the proximal shoulder 908 includes an outer, inclined edge 932 arranged between the proximal edge 924 and the outer edge 926 that is angled relative to the central longitudinal axis 910. As discussed further below with reference to FIGS. 21 and 22, each of the inclined edges 930 and 932 may be adapted to pivot towards the shaft 902 and about the proximal edge 924. In this way, at least a portion of the proximal shoulder 908 may be plastically deformable.

The flexible attachment of the proximal edge 924 to the shaft 902 may serve as a hinge, configured to enable a distal portion of the proximal shoulder 908 to turn about the proximal edge 924, such that the outer edge 926 may move radially towards or away from the shaft 902, while the distal edge 928 moves axially in a distal or proximal direction, respectively.

For example, in response to a radial force 934 acting on (e.g., pushing against, as shown in FIG. 20) the outer edge (e.g., surface) 926, the outer edge 926 may move radially inward, toward the shaft 902, thereby causing the distal edge 928 to move axially, in a distal direction toward the distal shoulder 904, and exert an axial force 936 on the proximal end 918 of the frame 914 of the valve 912. The radial force 934 may be referred to as a crimping force, exerted by a crimper or crimping device, and the axial force 936 may be referred to as a pushing force, exerted by the distal edge 928 of the proximal shoulder 908. FIGS. 21 and 22 show the different positions of the proximal shoulder 908 and valve 912 during application of these forces.

Prior to inserting the delivery device 900 into a lumen of a patient for delivery of the valve 912 to the target implantation site, the valve 912 may be crimped around the delivery device 900. For example, the valve 912 may be crimped around an inflatable balloon of the delivery device 900, between the distal shoulder 904 and the proximal shoulder 908. During crimping, the frame 914 of the valve 912 is radially compressed from an expanded state to an unexpanded or crimped state. Crimping of the valve 912 around the balloon may involve a crimping device (e.g., valve crimper) exerting inward, radial pressure against an outer surface of the frame 914, thereby forcing the frame 914 into a radially compressed state.

FIG. 20, as described above, shows the valve 912 and proximal shoulder 908 in an uncrimped state (e.g., position), prior to the crimping process. FIG. 21 shows the valve 912 and the proximal shoulder 908 in a partially crimped state and FIG. 22 shows the valve 912 and the proximal shoulder 908 in a fully crimped state.

Specifically, FIGS. 21 and 22 show a second cross-sectional view of the delivery device 900 (where the distal and proximal ends are flipped in the views of FIGS. 21 and 22, relative to FIG. 20), in a partially crimped configuration (FIG. 21) and a fully crimped configuration (FIG. 22). As shown in FIGS. 21 and 22, the delivery device 900 includes an inflatable balloon 940 surrounding a portion of the shaft 902, the distal shoulder 904, and the proximal shoulder 908. The valve 912 surrounds a valve-retaining portion 942 of the balloon 940, the valve-retaining portion 942 positioned between the distal shoulder 904 and the proximal shoulder 908.

A crimping device (e.g., valve crimper) may be arranged across both an outer surface of the frame 914 of the valve 912 and the outer edge 926 of the proximal shoulder 908. A portion of the delivery device 900, including the valve 912, arranged within the crimping device during a crimping process is denoted at 944. In this way, the outer edge 926 of the proximal shoulder 908 is adapted to interface with the crimping device.

As introduced above with reference to FIG. 20, during a crimping process, the crimping device exerts a radially inward, relative to the central longitudinal axis 910, force 934 (shown in FIG. 20) on the outer edge 926 and the outer surface of the frame 914. Since the proximal shoulder 908 is inclined relative to the central longitudinal axis 910 (e.g., at inclined edges 930 and 932), applying the radially directed force 934 causes the distal edge 928 to translate in a distal direction, toward the distal shoulder 904, and apply an axial push force 936 (see FIG. 20) on the proximal end 918 of the frame 914. The axial push force 936 urges the frame 914 in the distal direction towards the distal shoulder 904 and the nosecone 906 during crimping.

This may be seen by the change in position of the proximal shoulder 908 relative to the proximal end 918 of the frame 914 and the frame 914 relative to the distal shoulder 904 between FIGS. 21 and 22. For example, a distance, in the axial direction, between the distal edge 928 of the proximal shoulder 908 and the proximal edge 918 of the frame 914 is larger in the uncrimped or partially crimped state (FIG. 21) than in the fully crimped state (FIG. 22). Further, the distal end 920 of the frame 914 is arranged closer to (e.g., almost abuts) the proximal edge 922 of the distal shoulder 904 in the fully crimped state (FIG. 22) than in the uncrimped or partially crimped state (FIG. 21).

Since the proximal shoulder 908 may be plastically deformable and pivotable about the proximal edge 924, as the outer edge 926 moves radially inward during crimping, the distal edge 928 moves axially toward the distal shoulder, and the inclined edges 930 and 932 moved both radially inward and axially, in the distal direction. As a result, an angle of inclination 946 between the inner, inclined edge and the proximal edge 924 decreases and a total length 948 of the proximal shoulder 908, along the axial direction, increases as the proximal shoulder 908 is crimped further (e.g., from FIG. 21 to FIG. 22).

According to some embodiments, the proximal shoulder 908 may be configured (e.g., a geometry and material properties of the proximal shoulder may be selected) such that a distance between the distal edge 928 of the proximal shoulder 908 and the proximal edge 922 of the distal shoulder and/or nosecone, in the crimped state (as shown in FIG. 22), is substantially equal to the length of a crimped valve 912. As a result, a gap between the proximal end 922 of the distal shoulder 904 and the distal end 920 of the frame 914 may be reduced. This may arrange the frame 914 as close as possible to the nosecone 906, thereby minimizing gap formation therebetween during valve delivery to the target implantation site. As a result, direct contact between the distal end of the frame 914 and the inner walls of the sheath, during valve delivery, may be reduced, thereby reducing degradation to the sheath and/or valve.

In some embodiments, the proximal shoulder 908 may retain its crimped configuration (as shown in FIG. 22), after crimping is complete, for example, due to plastic deformation of the attachment at its proximal edge 924. As a result, the frame 914 may remain in close proximity to the nosecone 906 during valve delivery, as the delivery device 900 is advanced through the delivery sheath to the target implantation site. For example, in some embodiments, the proximal shoulder 908 can be made of a plastically deformable metal body (e.g., stainless steel) with an outer layer of a relatively softer material (e.g., silicone) covering the metal body. The metal body exhibits sufficient plastic deformation to retain its crimped configuration while the relatively softer material serves as an atraumatic covering.

According to some embodiments, the outer diameter of the proximal shoulder 908, in a crimped state (as shown in FIG. 22) may not be greater than the outer diameter of the crimped valve 912. In some embodiments, the outer edge 926 of the proximal shoulder 908 is flush with the outer surface of the frame 914 of the valve 912 in the crimped state.

In another embodiment, apices arranged at a distal end of a frame of a prosthetic valve may have a larger width that creates an increased radius of curvature (as compared to frames with narrower apices), thereby making the apices less sharp and creating a larger contact area that can reduce friction (and stress) between the apices and the sheath and/or native anatomy. As a result, during the delivery process, the frame may slide more easily through the sheath to the target implantation site and reduce a likelihood of causing degradation to the sheath and/or frame.

Figure 23:
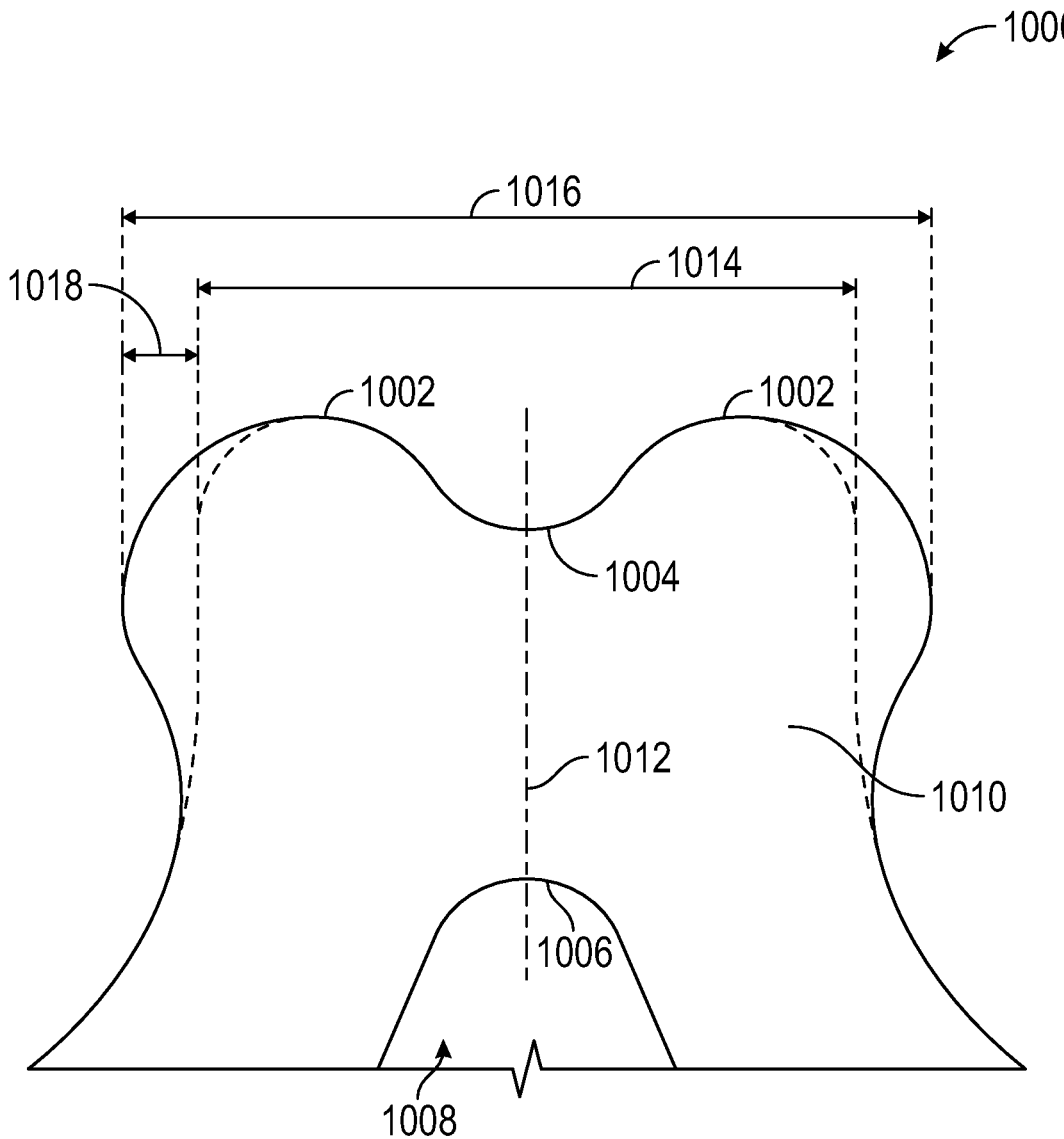
FIG. 23 is a schematic showing a single, distal apex of a frame of a prosthetic valve, the distal apex having a wider profile with an increased radius of curvature, according to an embodiment.

FIG. 23 shows an embodiment of a distal apex 1000 of a frame of a prosthetic heart valve having a wider profile with an increased radius of curvature (as compared to narrower apices). In some embodiments, a frame including the apex depicted in FIG. 23 may be used as the frame of the prosthetic heart valve 10 shown in FIG. 1 and/or prosthetic heart valve 50 shown in FIGS. 2A-2B. Additionally, in some embodiments, the "distal" apex 1000 may be a proximal apex of the frame of the prosthetic heart valve.

As shown in FIG. 23, the distal apex 1000 includes two arms, or struts, 1002, and a notch, or depression, 1004 arranged between and connecting the two arms 1002. Curved ends of the two arms 1002 may be the most distal elements (e.g., extending furthest in a distal direction) of the distal apex 1000. The notch 1004 is arranged opposite a cell end 1006 of an open cell 1008 of the frame. A mid-portion 1010 of the distal apex 1000 is arranged between the cell end 1006 and the notch 1004.

In some embodiments, as shown in FIG. 23, the two arms 1002 are arranged on opposite sides of a centerline 1012 of the distal apex 1000.

FIG. 23 shows an embodiment of the distal apex 1000 where an overall width of the apex 1000 is widened from a smaller, first width 1014 to a larger, second width 1016. For example, the distal apex 1000 may be a wider apex having the second width 1016 (shown by the solid lines in FIG. 23) as compared to a more "traditional" apex having the first width 1014 (shown by the dashed lines in FIG. 23). The increase in width on one side of the apex 1000, for one of the arms 1002, is shown by width 1018.

As shown in FIG. 23, increasing the width of each of the arms 1002 by width 1018, and the overall width of the distal apex 1000, results in a larger radius of curvature of the arms 1002 of the distal apex 1000. As a result, the distal apex 1000 is less sharp and has a larger surface area for contact with external structures (such as the sheath and/or native anatomy). As a result, when contacting external structures, such as the sheath, the wider and less sharp distal apex 1000 may have a lower coefficient of friction with the sheath and be less likely to cause degradation of the sheath.

In some embodiments, one or more features from the embodiments described herein may be combined to further reduce the likelihood of direct contact between the distal apices of the valve and inner walls of the delivery sheath, during a valve delivery process where the delivery device is being advanced through the delivery sheath to the target implantation site for the valve. For example, in one embodiment, the inwardly bent distal apices of the valve frame or the wider distal apices of the valve frame may be combined with the adjustable, proximal shoulder of the delivery device. In another embodiment, a delivery device including the nosecone jacket described herein may be combined with a crimped valve having inwardly curved distal apices. In yet another embodiment, a prosthetic heart valve may have distal apices that are inwardly curved relative to a central longitudinal axis and a bio-resorbable element may cover the inwardly curved distal apices. In still another embodiment, a delivery device having the adjustable, proximal shoulder described herein may be combined with a valve crimped on a valve retaining portion of the delivery device, the valve having distal apices with cushioning elements included thereon.

In this way, a prosthetic medical device (e.g., a prosthetic heart valve) and/or a delivery device adapted to delivery the prosthetic medical device to a target implantation site within a patient may be adapted with one or more elements that reduce direct contact and/or increase a contact surface area between a distal end of the prosthetic medical device and a delivery sheath through which the delivery device is routed within the patient, to the target implantation site. As a result, abrasion of inner walls of the delivery sheath may be reduced and degradation to the sheath and/or prosthetic medical device may be reduced during a device delivery process. In one example, the distal end of the prosthetic medical device may be arranged proximate to a nosecone of the delivery device and the delivery device and/or prosthetic medical device may be adapted to reduce a gap between the distal end of the prosthetic medical device and a proximal end of the nosecone. This may further reduce the likelihood of the prosthetic medical device and delivery sheath having direct contact with one another during maneuvering of the prosthetic medical device, via the delivery device, through the sheath and patient to the target implantation site. In some embodiments, the distal end of the prosthetic medical device may include a plurality of distal apices. One or more of the delivery device and/or prosthetic valve embodiments described herein may be configured to cover or shield the distal apices from having direct contact with inner walls of the sheath. As a result, the integrity of the sheath and/or prosthetic medical device may be maintained.

General Considerations

It should be understood that the disclosed embodiments can be adapted to deliver and implant prosthetic devices in any of the native annuluses of the heart (e.g., the pulmonary, mitral, and tricuspid annuluses), and can be used with any of various delivery approaches (e.g., retrograde, antegrade, transseptal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used herein, with reference to the transcatheter delivery system, the prosthetic heart valve, the delivery device, the balloon catheter, the introducer sheath (e.g., the delivery sheath), the balloon shoulder assembly, and the balloon shoulders, "proximal" refers to a position, direction, or portion of a component that is closer to a handle of the delivery system that is outside the patient, while "distal" refers to a position, direction, or portion of a component that is further away from the handle (and farther into a body of the patient). The terms "longitudinal" and "axial" refer to an axis extending in the proximal and distal directions, unless otherwise expressly defined.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and or.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A prosthetic heart valve, comprising:
a radially expandable and compressible frame including a first end with a plurality of apices spaced apart from one another around a circumference of the first end;
a plurality of leaflets secured to one another at their adjacent sides to form a plurality of commissures spaced circumferentially apart from each other, wherein the plurality of commissures is coupled to the frame, and wherein at least one apex of the plurality of apices is disposed circumferentially between two adjacent commissures of the plurality of commissures and spaced circumferentially away from each commissure of the two adjacent commissures; and
a plurality of discrete cushioning elements covering the plurality of apices, wherein each cushioning element of the plurality of cushioning elements is coupled to and covers a different apex of the plurality of apices, wherein each apex comprises an axially facing surface forming a tip of the apex, and wherein each cushioning element extends radially across and covers the axially facing surface of a corresponding apex.

2. The prosthetic heart valve of claim 1, wherein each cushioning element comprises a flexible material folded over the axially facing surface of the corresponding apex of the plurality of apices.

3. The prosthetic heart valve of any one of the preceding claims, wherein each cushioning element comprises a plurality of folds arranged over and across the axially facing surface of the corresponding apex of the plurality of apices.

4. The prosthetic heart valve of claim 3, wherein, for each cushioning element, the plurality of folds extends between an inner layer and an outer layer of the cushioning element, the inner layer covering an inner surface of the corresponding apex and the outer layer covering an outer surface of the corresponding apex, the inner and outer surfaces relative to a central longitudinal axis of the prosthetic heart valve.

5. The prosthetic heart valve of claim 4, wherein the inner layer and the outer layer are secured together around both sides of the corresponding apex.

6. A prosthetic heart valve, comprising:
a frame including a first end with a plurality of apices spaced apart from one another around a circumference of the first end; and
a plurality of discrete cushioning elements covering the plurality of apices, wherein each cushioning element of the plurality of cushioning elements is coupled to and covers a different apex of the plurality of apices, wherein each cushioning element comprises an inner layer covering an inner surface of a corresponding apex of the plurality of apices, an outer layer covering an outer surface of the corresponding apex, and a distal layer defining a distal surface of the cushioning element and extending radially from the inner layer to the outer layer and across a distal edge of the corresponding apex.

7. The prosthetic heart valve of claim 6, wherein each cushioning element further comprises a plurality of folds arranged between the inner layer and the outer layer, and wherein each fold of the plurality of folds extends from the distal layer to a base of the corresponding apex.

8. The prosthetic heart valve of claim 1, wherein each cushioning element comprises one or more sutures repeatedly looped over a corresponding apex of the plurality of apices.

9. The prosthetic heart valve of claim 1, wherein each cushioning element comprises a pocket surrounding a corresponding apex of the plurality of apices and including a padding element disposed within the pocket, the padding element arranged distally to the axially facing surface of the corresponding apex.

10. The prosthetic heart valve of claim 9, wherein overlapping folds of the pocket are secured to one another, along at least a portion of a periphery of the pocket, and wherein the pocket is fastened directly to the corresponding apex.

11. A prosthetic heart valve, comprising:
a radially compressible and expandable frame including a first end with a plurality of apices spaced apart from one another around a circumference of the first end;
a plurality of leaflets secured to one another at their adjacent sides to form a plurality of commissures spaced circumferentially apart from each other, wherein the plurality of commissures is coupled to the frame, and wherein at least one apex of the plurality of apices is disposed circumferentially between two adjacent commissures of the plurality of commissures and spaced circumferentially away from each commissure of the two adjacent commissures; and a plurality of discrete cushioning elements covering the plurality of apices, wherein each cushioning element of the plurality of cushioning elements is coupled to and covers a different apex of the plurality of apices, and wherein each cushioning element comprises fabric.

12. The prosthetic heart valve of claim 11, wherein each cushioning element covers an axially facing surface of a corresponding apex of the plurality of apices that defines a tip of the apex.

13. The prosthetic heart valve of claim 11, wherein each cushioning element comprises a plurality of folds arranged over and extending continuously across, in a radial direction, a distal-most edge of a corresponding apex of the plurality of apices.

14. The prosthetic heart valve of claim 11, wherein each cushioning element comprises an inner layer covering an inner surface of a corresponding apex of the plurality of apices, an outer layer covering an outer surface of the corresponding apex, and a distal layer defining a distal surface of the cushioning element and extending between the inner layer and the outer layer and across a distal edge of the corresponding apex, and wherein the inner and outer layers extend from the distal surface to a base of the corresponding apex, the base connected to ends of two adjacent angled struts of the frame.

15. The prosthetic heart valve of claim 11, wherein each cushioning element is fixed to a corresponding apex of the plurality of apices.

* * * * *